United States Patent
Pallas et al.

(10) Patent No.: US 10,994,275 B2
(45) Date of Patent: **\*May 4, 2021**

(54) SYSTEMS AND METHODS FOR BIOLOGICAL ANALYSIS

(71) Applicant: LIFE TECHNOLOGIES CORPORATION, Carlsbad, CA (US)

(72) Inventors: Michael Pallas, San Bruno, CA (US); Evan Foster, San Mateo, CA (US); Jorge Fonseca, East Palo Alto, CA (US); James Nurse, Westport, WA (US); Theodore Straub, Burlingame, CA (US)

(73) Assignee: LIFE TECHNOLOGIES CORPORATION, Carlsbad, CA (US)

(\*) Notice: Subject to any disclaimer, the term of this patent is extended or adjusted under 35 U.S.C. 154(b) by 144 days.

This patent is subject to a terminal disclaimer.

(21) Appl. No.: 16/291,757

(22) Filed: Mar. 4, 2019

(65) Prior Publication Data
US 2019/0201891 A1 Jul. 4, 2019

Related U.S. Application Data

(63) Continuation of application No. 14/893,356, filed as application No. PCT/US2014/039623 on May 27, 2014, now Pat. No. 10,252,272.

(Continued)

(51) Int. Cl.
*B01L 3/00* (2006.01)
*B01L 7/00* (2006.01)
(Continued)

(52) U.S. Cl.
CPC ....... *B01L 3/50851* (2013.01); *B01L 3/50857* (2013.01); *B01L 7/52* (2013.01);
(Continued)

(58) Field of Classification Search
None
See application file for complete search history.

(56) References Cited

U.S. PATENT DOCUMENTS

| 2002/0001546 A1 | 1/2002 | Hunter et al. |
| 2008/0000892 A1 | 1/2008 | Hirano et al. |

(Continued)

FOREIGN PATENT DOCUMENTS

| GB | 2472321 | 2/2011 |
| WO | 2013049659 | 4/2013 |

(Continued)

OTHER PUBLICATIONS

PCT/US2014/039623, International Search Report and Written Opinion dated Sep. 29, 2014, 12 pages.

(Continued)

*Primary Examiner* — Matthew D Krcha
(74) *Attorney, Agent, or Firm* — Jones Robb, P.L.L.C.

(57) ABSTRACT

A system for processing a plurality of biological samples contains a support and a temperature controller. The suppose is configured to hold a case that includes an inner chamber and a substrate located within the inner chamber, the substrate containing a plurality of isolated reaction sites containing one or more biological samples. The temperature controller is configured to maintain or control a temperature of at least one of the support, the case, or the one or more biological samples during an assay or reaction on the one or more biological samples. The support is also configured to maintain at least one of the surfaces of substrate at a positive angle relative to a horizontal plane during the assay or reaction.

20 Claims, 19 Drawing Sheets

Related U.S. Application Data

(60) Provisional application No. 61/827,477, filed on May 24, 2013.

(51) Int. Cl.
  *B01L 9/00* (2006.01)
  *C12Q 1/686* (2018.01)
  *G01N 21/64* (2006.01)

(52) U.S. Cl.
  CPC .............. *B01L 9/523* (2013.01); *C12Q 1/686* (2013.01); *B01L 2200/0673* (2013.01); *B01L 2200/0684* (2013.01); *B01L 2200/141* (2013.01); *B01L 2300/0609* (2013.01); *B01L 2300/0819* (2013.01); *B01L 2300/0822* (2013.01); *B01L 2300/0829* (2013.01); *B01L 2300/0893* (2013.01); *B01L 2300/18* (2013.01); *G01N 21/6452* (2013.01)

(56) References Cited

U.S. PATENT DOCUMENTS

| | | |
|---|---|---|
| 2009/0010811 A1 | 1/2009 | Chan et al. |
| 2011/0152108 A1* | 6/2011 | Brenan .................... B01L 7/52 506/7 |
| 2013/0031890 A1 | 2/2013 | Shovels et al. |
| 2013/0032002 A1 | 2/2013 | Kuentzel |
| 2013/0032107 A1 | 2/2013 | Nasto et al. |
| 2013/0032242 A1 | 2/2013 | Beranger et al. |

FOREIGN PATENT DOCUMENTS

| | | |
|---|---|---|
| WO | 2013049709 | 4/2013 |
| WO | 2013138685 | 9/2013 |
| WO | 2013138706 A2 | 9/2013 |
| WO | 2013138724 A2 | 9/2013 |
| WO | 2013138746 | 9/2013 |
| WO | 2013138767 | 9/2013 |
| WO | 2014074740 | 5/2014 |

OTHER PUBLICATIONS

PCT/US2014/039623, International Preliminary Report on Patentability dated Dec. 3, 2015, 9 pages.

\* cited by examiner

SYSTEMS AND METHODS FOR BIOLOGICAL ANALYSIS

CROSS-REFERENCE TO RELATED APPLICATIONS

This application is a continuation of U.S. patent application Ser. No. 14/893,356, filed Nov. 23, 2015, which is a U.S. National Application filed under 35 U.S.C. § 371 of International Application No. PCT/US2014/039623, filed May 27 2014, which claims the benefit of priority of U.S. Provisional Application No. 61/827,477, filed on May 24, 2013, each of which is incorporated herein by reference in its entirety.

BACKGROUND OF THE INVENTION

Field of the Invention

The present invention relates generally to systems, devices, and methods for observing, testing, and/or analyzing one or more biological samples, and more specifically to systems, devices, and methods for observing, testing, and/or analyzing an array of biological samples.

Description of the Related Art

Systems for biological and biochemical reactions have been used to monitor, measure, and/or analyze such reactions in real time and during post-run or end-point analysis. Such systems may include optical reader, which are commonly used in sequencing, genotyping, polymerase chain reaction (PCR), and other biochemical reactions to monitor the progress and provide quantitative data. For example, an optical excitation beam may be used in real-time PCR (qPCR) reactions to illuminate hybridization probes or molecular beacons to provide fluorescent signals indicative of the amount of a target gene or other nucleotide sequence. In addition, end-point optical reader may be used to provide data after reactions have completed, such as for digital PCR (dPCR) analysis. Increasing demands to provide greater numbers of reactions per test or experiment have resulted in instruments that are able to conduct ever higher numbers of reactions simultaneously.

The increase in the number sample sites in a test or experiment has led to microtiter plates and other sample formats that provide ever smaller sample volumes. In addition, techniques such as digital PCR (dPCR) have increased the demand for smaller sample volumes that contain either zero or one target nucleotide sequence in all or the majority of a large number of test samples. There is a need for systems and sample formats that will provide reliable data in a high-density sample format.

BRIEF DESCRIPTION OF THE DRAWINGS

Embodiments of the present invention may be better understood from the following detailed description when read in conjunction with the accompanying drawings. Such embodiments, which are for illustrative purposes only, depict novel and non-obvious aspects of the invention. The drawings include the following figures.

DETAILED DESCRIPTION OF THE DRAWINGS

Figure 1:
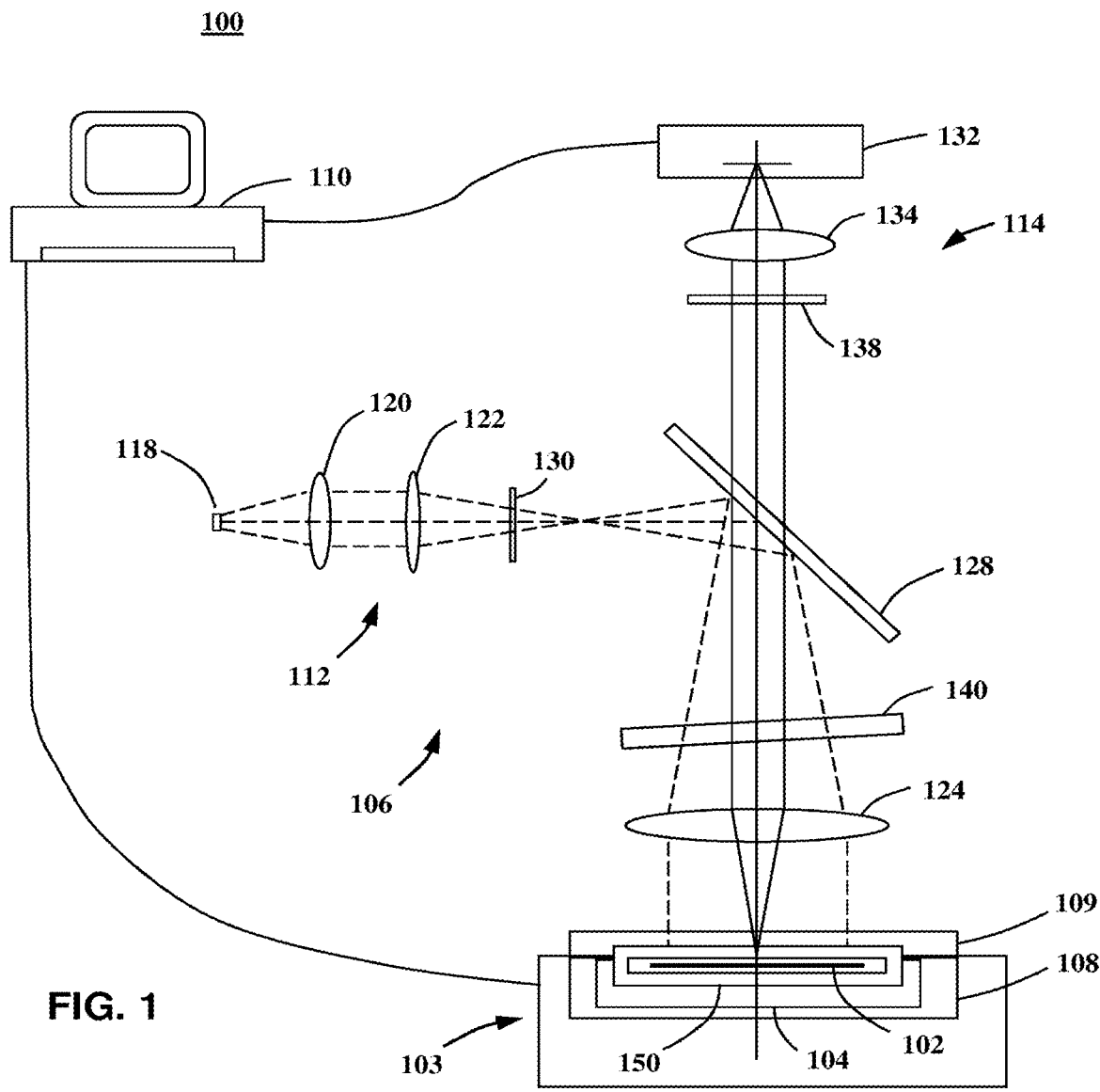
FIG. 1 is a system for processing a plurality of biological samples according to embodiments of the present invention.

Embodiments of the present invention are generally directed devices, instruments, systems, and methods for monitoring or measuring a biological reaction for a large number of small samples or solutions. Embodiments include the use of a polymerase chain reaction (PCR) processes or protocol, which may include, without limitation, allele-specific PCR, asymmetric PCR, ligation-mediated PCR, multiplex PCR, nested PCR, real-time PCR (qPCR), genome walking, bridge PCR, digital PCR (dPCR), or the like.

While devices, instruments, systems, and methods according to embodiments of the present invention are applicable to any PCR processes or protocols where a large number of samples or solutions are processed, embodiments of the present invention are particularly well suited for dPCR. In dPCR, a solution containing a relatively small number of a target polynucleotide or nucleotide sequence is subdivided into a large number of very small test samples or volumes, such that the vast majority of these samples or volumes contain either one molecule of the target nucleotide sequence or none of the target nucleotide sequence. When the samples are subsequently thermally cycled in a PCR protocol, procedure, or experiment, the sample containing the target nucleotide sequence are greatly amplified and produce a positive detection signal, while the samples containing no target nucleotide sequence are not amplified and produce no detection signal or a signal that is below a predetermined threshold. Using Poisson statistics, the number of target nucleotide sequences in the original solution may be correlated to the number of samples producing a positive detection signal. In some embodiments, both qPCR and dPCR processes or protocols are conducted using the same devices, instruments, systems, and methods.

In various embodiments, the devices, instruments, systems, and methods described herein may be used to detect one or more types of biological components of interest contained in a sample or solution containing the biological components of interest. These biological components of interest may be any suitable biological target including, but are not limited to, DNA sequences (including cell-free DNA), RNA sequences, genes, oligonucleotides, molecules, proteins, biomarkers, cells (e.g., circulating tumor cells), or any other suitable target biomolecule. In various embodiments, such biological components may be used in conjunction with various PCR methods and systems in applications such as fetal diagnostics, multiplex dPCR, viral detection and quantification standards, genotyping, sequencing validation, mutation detection, detection of genetically modified organisms, rare allele detection, and copy number variation.

According to embodiments of the present invention, samples or solutions containing biological targets may be contained in a small sample volume or reaction volume. The samples or solutions for embodiments of the present invention disclosed herein are generally illustrated as being contained in through-holes located in a substrate material; however, other forms of sample or reaction sites may be used, including reaction volumes located within wells or indentations formed in a substrate, spots of solution distributed on the surface a substrate, or other types of reaction chambers or formats, such as samples or solutions located within test sites or volumes of a microfluidic system, or within or on small beads or spheres.

In order to conduct a dPCR protocol, procedure, process, or experiment according to embodiments of the present invention, an initial sample or solution may be divided into tens of thousands, hundreds of thousands, or even millions of reaction sites or regions, each having a volume of a few nanoliters, about one nanoliter, or less than one nanoliter (e.g., 10's or 100's of picoliters or less), in a way that is simple and cost effective. Because the number of target nucleotide sequences may be very small, it may also be important in such circumstances that the entire content of the initial solution be accounted for and contained in one of the sample volumes or chambers being processed. For example, where there are only a few target nucleotides present in the initial solution, many or all of these target nucleotide could potentially be contained in a small residual fluid volume that is not successfully loaded into one of the reaction sites or regions. Thus, efficient transfer of the initial solution helps reduces the chances of a miscalculation in the number count of a rare allele or target nucleotide or, even worse, of missing the rare allele or target nucleotide altogether because none of these targets were distributed into one of the designated reaction sites or regions. Accordingly, embodiments of the present invention may be used to efficiently distribute and load an initial sample solution into a large number of reaction sites or regions or through-holes in a way that results in all, or essentially all, of the sample or solution being contained in one of a predetermined reaction sites.

Referring to FIG. 1, a system 100 for biological analysis comprises a sample holder, substrate, or plate 102 configured to hold a plurality of biological samples. In certain embodiments, system 100 may further comprise any or all of a carrier, support, or support frame 104 for retaining, locating, and/or supporting sample holder 102, a base or mount 103 for receiving the sample holder 102, an optical system 106 for monitoring and/or measuring one or more biological processes of the biological samples, a thermal controller 108 for maintaining and/or cycling a thermal environment of the biological samples and/or sample holder 102, a heated lid 109 disposed above the sample holder for control of the environment about or within the biological samples and/or sample holder 102, and one or more electronic processors 110 with associated electronic memory and algorithms for controlling, monitoring, and/or measuring the one or more biological processes occurring in the biological samples. In various embodiments, system 100 comprises an instrument including a combination of some or all of carrier 104, base 103, optical system 106, thermal controller 108, heated lid 109, and/or one or more the electronic processors 110.

In certain embodiments, system 100 and sample holder 102 are suitable for performing real-time PCR processes on a plurality of biological samples. In other embodiments, system 100 and sample holder 102 are suitable for performing other biological or biochemistry processes such as sequencing or genotyping measurements. In the illustrated embodiment, optical system 106 comprises an excitation system 112 for illuminating sample holder 102 and the associated biological samples, and an emission optical system 114 for receiving emissions from the biological samples, for example, due to fluorescent signals produced by one or more fluorescent dyes or probe molecules present in the biological samples and in response to an excitation beam. Excitation optical system 112 includes an excitation source 118, lenses 120, 122, 124, beamsplitter 128. Excitation optical system 112 may also include one or more optical filters 130 for limiting the wavelength range of light received by the biological samples. Emission optical system 114 includes optical sensor 132, lenses 124, 134, beamsplitter 128. Emission optical system 114 may also include one or more optical filters 138 for limiting the wavelength range of light received by optical sensor 132. In addition, optical system 106 may include one or more windows 140 configured to isolate portions of system 100, for example, to reduce or eliminate unwanted thermal or optical effects during processing of the biological samples.

In certain embodiments, sample holder 102 is disposed within an enclosure, housing, or case 150 that may be sealed, for example, to reduce or prevent evaporation of the biological samples. In certain embodiments, one or more sample holders 102 or sample cases 150 are retained, located and/or supported by carrier 104 configured for aligning and/or transporting the sample holder 102 within system 100.

Figure 2:
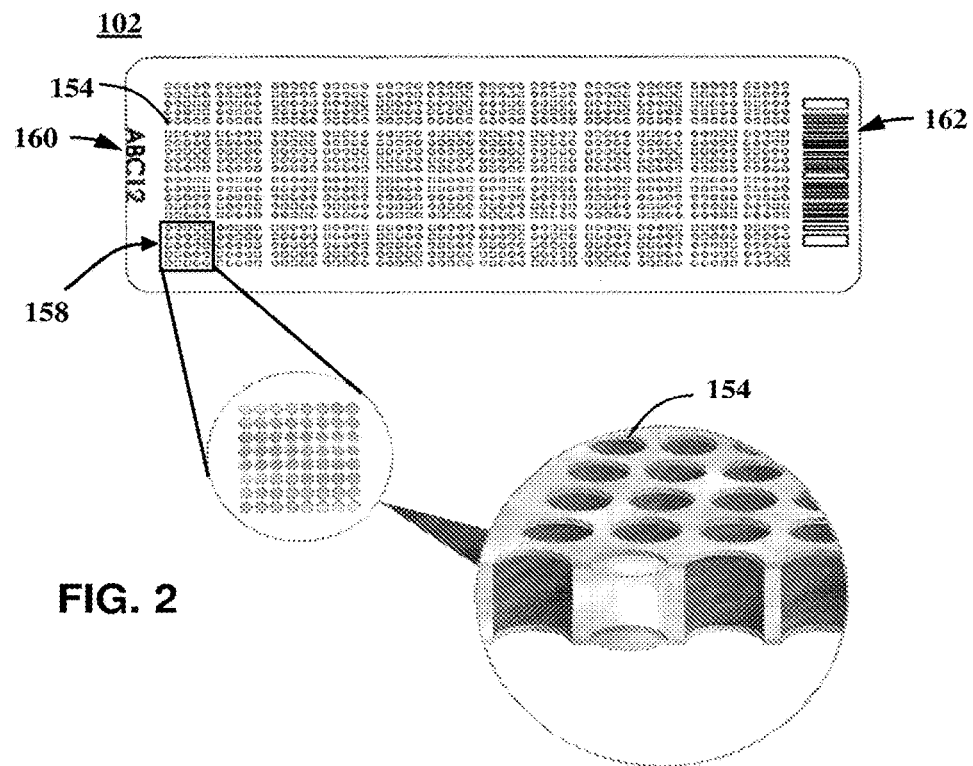
FIG. 2 is a sample holder according to an embodiment of the present invention comprising a plurality of through-holes.

Referring to FIG. 2, sample holder 102 may include a substrate comprising opposing surfaces and a plurality of reaction regions, wells, or vials 154 disposed over one or both surfaces. In the illustrated embodiment shown in FIG. 2, reaction regions 154 comprise a plurality of through-holes disposed between the opposing surfaces of sample holder 102. In certain embodiments, through-holes 154 are evenly spaced from one another along a two-dimensional array. Alternatively, through-holes 154 may be grouped in a plurality of subarrays 158, for example, to facilitate loading of samples into different groups of through-holes. For example, in the illustrated embodiment shown in FIG. 2, sample holder 102 comprises 4 by 12 subarrays, where each subarray comprises 8 by 8 individual through holes 154, for a total of 3072 through-holes 154 on sample holder 102. Through-holes 154 may be dimensioned such that a liquid containing a biological sample and/or reference dye is held within through-holes 154 by surface tension or capillary forces, as illustrated in the magnified view of FIG. 2. This effect may be enhanced by coating the walls of through-holes 154 with a hydrophilic coating. In certain embodiments, the outer surfaces of sample holder 102 comprise a hydrophobic material or coating configured to reduce or eliminate cross-contamination or mixing between the samples located in the various through-holes 154. Various aspects and advantages of a through-hole arrangement for supporting biological samples are further disclosed in U.S. Pat. Nos. 6,306,578; 6,893,877; 7,682,565, the entire contents of each of which patents are hereby incorporated by reference in their entirety for all purposes as if fully set forth herein.

In certain embodiments, an initial sample or solution for a sample holder, such as sample holder 102, may be divided into hundreds, thousands, tens of thousands, hundreds of thousands, or even millions of reaction sites or regions, each having a volume of, for example, a few nanoliters, about one nanoliter, or less than one nanoliter (e.g., 10's or 100's of picoliters or less).

In the illustrated embodiment shown in FIG. 2, sample holder 102 has a rectangular shape; however, sample holder 102 may have other shapes, such as a square or circular shape. In certain embodiments, sample holder 102 has a square shape and an overall dimension of 15 millimeter by 15 millimeter. In such embodiments, sample holder 102 may have an active area, region, or zone with a dimension of 13 millimeter by 13 millimeter. As used herein, the terms "active area", "active region", or "active zone" mean a surface area, region, or zone of a sample holder, such as the sample holder 102, over which reaction regions, through-holes, or solution volumes are contained or distributed. In certain embodiments, the active area of sample holder 102 may be increased to 14 millimeter by 14 millimeter or larger, for example, a 15 millimeter by 15 millimeter substrate dimension.

In the illustrated embodiment of FIG. 2, through-holes 154 may have a characteristic diameter of 320 micrometer and a pitch of 500 micrometers between adjacent through-holes. In other embodiments, through-holes 154 have a characteristic diameter of 75 micrometer and have a pitch of 125 micrometers between adjacent through-holes. In yet other embodiments, through-holes 154 have a characteristic diameter of that is less than or equal 75 micrometers, for example, a characteristic diameter that is less or equal to 60 micrometers or less or equal to 50 micrometers. In other embodiments, through-holes 154 have a characteristic diameter that is less than or equal to 20 micrometers, less than or equal to 10 micrometers, or less than or equal to 1 micrometer. The pitch between through-holes may be less than or equal to 125 micrometers, for example, less than or equal to 100 micrometers, less than or equal to 30 micrometers, or less than or equal to 10 micrometers.

In certain embodiments, sample holder 102 comprises a substrate having a thickness between the opposing surfaces of sample holder 102 that is at or about 300 micrometer, wherein each through-hole 154 may have a volume of or about 1 nanoliter, 33 nanoliters, or somewhere between 1.3 nanoliter and 33 nanoliters. Alternatively, the volume of each through-holes 154 may be less than or equal to 1 nanoliter, for example, by decreasing the diameter of through-holes 154 and/or the thickness of sample holder 102 substrate. For example, each through-holes 154 may have a volume that is less than or equal to 1 nanoliter, less than or equal to 100 picoliters, less than or equal to 30 picoliters, or less than or equal to 10 picoliters. In other embodiments, the volume some or all of the through-holes 154 is in a range from 1 nanoliter to 20 nanoliters. In certain embodiments, sample holder 102 comprises a substrate that is similar to or equal to a substrate described in copending U.S. patent application No. 61/612,087, PCT application number PCT/US2013/032002, U.S. provisional application No. 61/723,759, or PCT application number PCT/US2013/032002, each of which applications are herein incorporated by reference in their entirety. For example, through-holes 154 may have a hexagonal shape or be arranged in a hexagonal pattern. In addition, the array of through-holes 154 can be arranged to have drop-outs in the hole pattern, as discussed in U.S. provisional application No. 61/723,759 or PCT application number PCT/US2013/032002.

In certain embodiments, the density of through-holes 154 is at least 100 through-holes per square millimeter. Higher densities are also anticipated. For example, a density of through-holes 154 may be greater than or equal to 150 through-holes per square millimeter, greater than or equal to 200 through-holes per square millimeter, greater than or equal to 500 through-holes per square millimeter, greater than or equal to 1,000 through-holes per square millimeter, or greater than or equal to 10,000 through-holes per square millimeter.

Advantageously, all the through-holes 154 with an active area may be simultaneously imaged and analyzed by an optical system. In certain embodiments, active area comprises over 12,000 through-holes 154. In other embodiments, active area comprises at least 20,000, at least 30,000, at least 100,000, at least 1,000,000 through-holes, or at least 10,000,000 through-holes.

In certain embodiments, through-holes 154 comprise a first plurality of the through-holes characterized by a first characteristic diameter, thickness, or volume and a second plurality of the through-holes characterized by a second characteristic diameter, thickness, or volume that is different than the first characteristic diameter, thickness, or volume. Such variation in through-hole size or dimension may be used, for example, to simultaneously analyze two or more different nucleotide sequences that may have different concentrations. Additionally or alternatively, a variation in through-hole 154 size on a single substrate 102 may be used to increase the dynamic range of a process or experiment. For example, sample holder 102 may comprise two or more subarrays of through-holes 154, where each group is characterized by a diameter or thickness that is different a diameter or thickness of the through-holes 154 of the other or remaining group(s). Each group may be sized to provide a different dynamic range of number count of a target polynucleotide. The subarrays may be located on different parts of substrate 102 or may be interspersed so that two or more subarrays extend over the entire active area of sample holder 102 or over a common portion of active area of sample holder 102.

In certain embodiments, at least some of the through-holes 154 are tapered or chamfered over all or a portion of their walls. The use of a chamfer and/or a tapered through-holes have been found to reduce the average distance or total area between adjacent through-holes 154, without exceeding optical limitations for minimum spacing between solution sites or test samples. This results in a reduction in the amount liquid solution that is left behind on a surface of substrate 102 during a loading process. Thus, higher loading efficiency may be obtained, while still maintaining a larger effective spacing between adjacent solution sites or test samples for the optical system.

In the illustrated embodiment shown in FIG. 2, sample holder 102 may also comprise alphanumeric characters 160, a barcode 162, or other symbolic representations from which information relative to an individual holder 102 may be derived or ascertained. Such information includes, but is not limited to, reagents contained with some or all of the through-holes 154 and/or protocols to be followed when using sample holder 102. In certain embodiments, emission optical system 114 is configured so that optical sensor 132 may be used to read characters 160 and/or barcode 162. In addition, emission optical system 114 may be configured to provide images that contain, in a single frame, portions of sample holder 102 containing through-holes 154 and either, or both, alphanumeric characters 160 or a barcode 162. In some embodiments, emission optical system 114 is configured to provide images that contain, in a single frame, portions of two or more sample holders 102 containing through-holes 154 for each sample holder 102 and either, or both, alphanumeric characters 160 or a barcode 162 the same sample holders 102.

Figure 3:
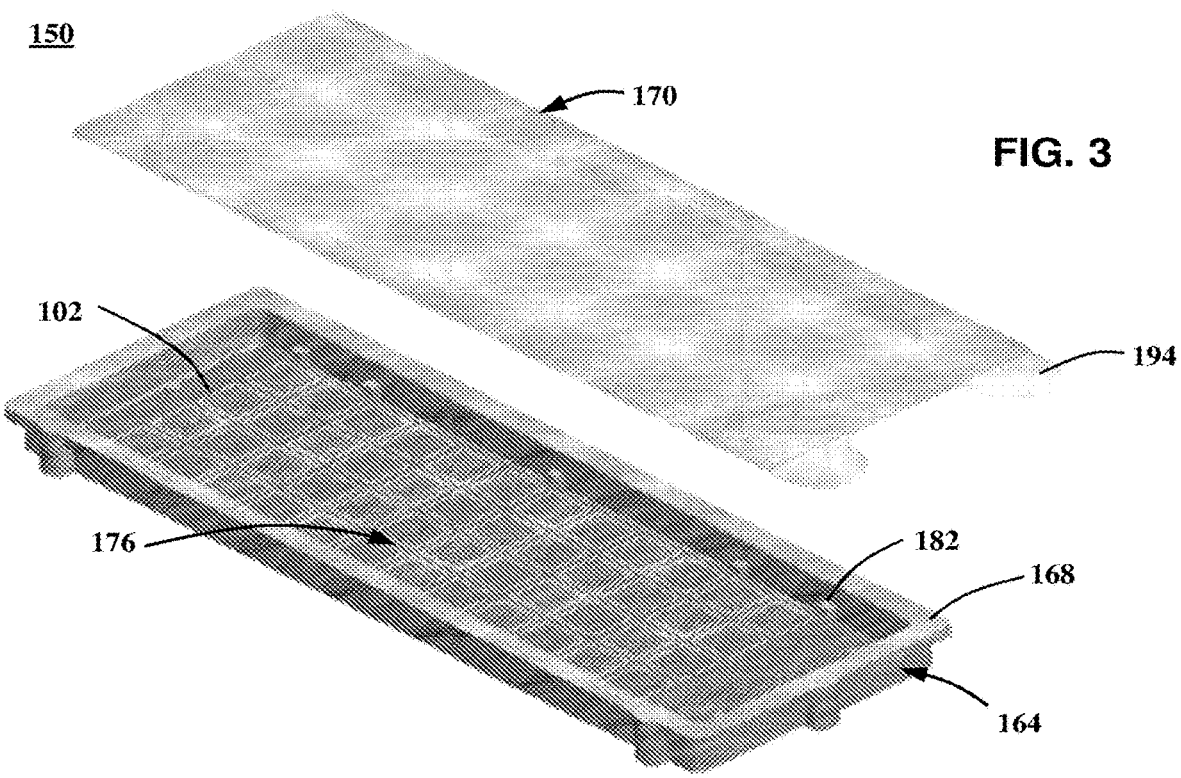
FIG. 3 is a perspective view of a case according to an embodiment of the present invention containing the sample holder shown in FIG. 2.
Figure 4:
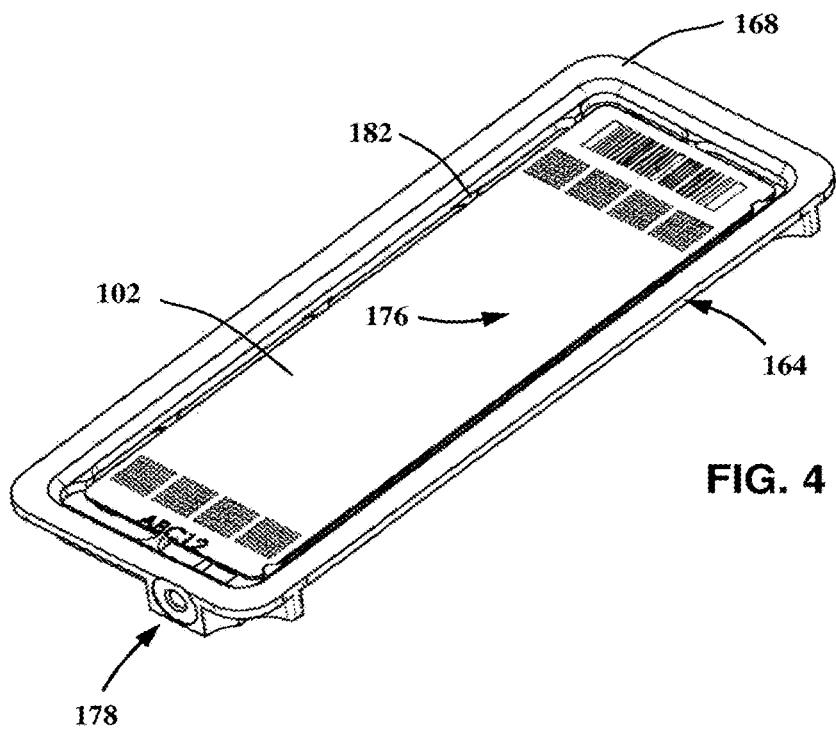
FIG. 4 is a perspective view of a base of the case according to an embodiment of the present invention containing the sample holder shown in FIG. 2.
Figure 5:
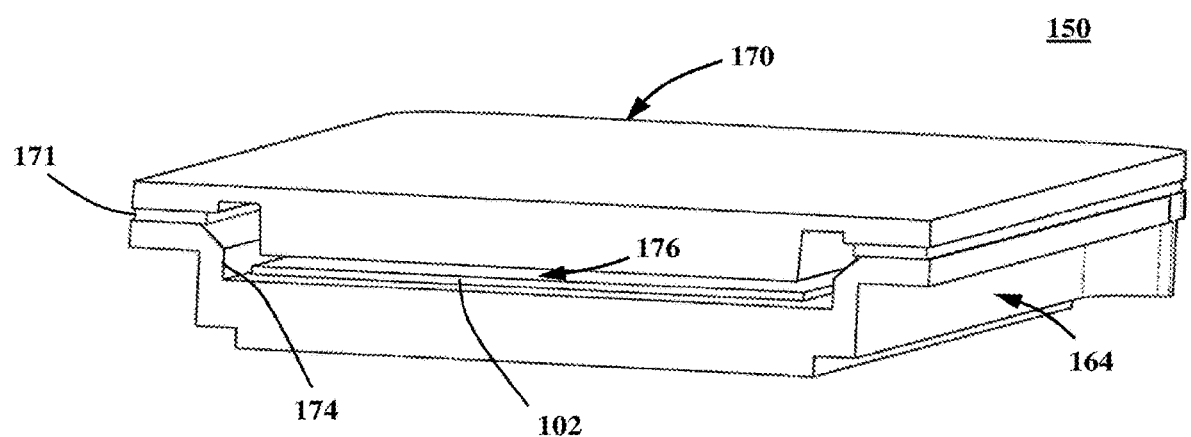
FIG. 5 is a cross-section view of a case according to an embodiment of the present invention showing a sample holder disposed between a base and a cover.

Referring to FIG. 3, in certain embodiments, case 150 comprises a base 164 having a top surface 168 and a cover 170 that sealably engages top surface 168 of base 164 to form an enclosure for containing sample plate 102 so as to at least partially isolate or separated the biological samples from an outside environment. Case 150 may also optionally comprise a gasket or seal 171 located between base 164 and cover 170. With further reference to FIGS. 4-8, base 164 comprises a bottom surface 172 and side walls 174 that, together with cover 170, form a cavity, chamber, inner chamber, or enclosure 176 with sufficient depth to contain sample plate 102 completely inside cavity 176 and entirely below top surface 168 and cover 170, as illustrated in FIG. 5. Base 164 may further comprise one or more fill ports 178 for injecting fluid into cavity 176 after cover 170 is attached to base 164. Bottom surface 172 may comprise a completely or generally flat surface. Alternatively, bottom surface 172 may include one or more indentations 180. For example, in the illustrated embodiment shown in FIG. 5, indentation 180 is located proximal to fill port 178 and is configured to provide an enlarged working volume for allowing fluid to enter and air to exit as cavity 176 is filled with a liquid using a pipette or similar device.

In certain embodiments, the sealed case 150 is injected through fill port 178 with a sealing fluid or liquid that is hydrophobic in nature, which favorably seals, but does not mix with, biological samples that are more hydrophilic. The use of such a sealing fluid or liquid into case 150 may be used to further seal the biological samples within through-holes 154 and reduce or eliminate evaporation of the biological sample during thermal cycling at high temperatures (e.g., upper temperatures from 90 to 100 degree. C.). A suitable sealing fluid includes, but is not limited to, Fluorinert™, sold commercially by 3M Company, for example, perfluorohexane ($C_6F_{14}$).

Base 164 may also comprise a plurality of bosses, tabs, staking sites, or support pads 182 located above and/or integral with bottom surface 172. Support pads 182 may be configured to engage and secure sample holder 102. Alternatively, some of the support pads 182 may be configured to simply contact or support sample holder 102 along its length, for example, to reduce or prevent warping or bending of sample holder 102. Support pads 182 may additionally be configured to maintain a predetermined spacing between the bottom surface of sample holder 102 and bottom surface 172 of base 164. The number of support pads 182 may be selected to maintain a predetermined flatness of sample holder 102 when engaged by some or all of support pads 182. In certain embodiments, some of support pads 182 engage sample plate 102 in a lateral direction (e.g., along a plane parallel to bottom surface 172), while the remaining support pads 182 are configured to contact sample plate 102 only along a bottom face of plate 102. In other embodiments, sample plate 102 is engaged by at least some of support pads 182 through the use of a tool or fixture to displace some of the material of a support pad 182 in a lateral direction. In other embodiments, engagement between plate 102 and at least some of the support pads 182 is provide by use of an adhesive, epoxy, or weld material disposed between sample plate 102 and support pads 182.

In certain embodiments, in addition to or in place of the plurality of support pads 182, base 164 comprises a one or more rails configured to receive a peripheral portion of sample holder 102. For example, a pair of rails may be disposed along opposite side walls 174. The rails may be disposed along the entire length of each side wall 174. Alternatively, the rails may be disposed along only a portion of each side wall 174. In addition, one or more support pads 182 may be included along the opposite side walls 174 and/or along other walls 174 of base 164.

Base 164 may be made of a material having a relatively high thermal conductivity and/or a high thermal diffusivity, for example, a material having a thermal conductivity of at least 50 to 200 $W·m^{-1}·K^{-1}$ and/or a thermal diffusivity of at least about $8×10^{-5} m^2·s^{-1}$. Suitable materials include, but are not limited to metallic materials such as aluminum, copper, silver, or gold, or a semimetal such as graphite. Use of such materials assist in providing a uniform temperature (low thermal non-uniformity or TNU) or predetermined temperature profile bottom surface 172 of base 164, which in turn provides an uniform or predetermined temperature profile over sample holder 102.

In certain embodiments, provision of a low TNU or predetermined temperature profile over sample holder 102 is further enhanced by locating the bottom surface of sample holder 102 close to bottom surface 172 of base 164, while simultaneously preventing contact between bottom surface 172 and sample holder 102 over the entire extent of sample holder 102. To meet these conditions, in certain embodiments, sample holder 102 is disposed a nominal distance of less than 300 micrometers from the bottom surface 172 of base 164. In other embodiments, the nominal distance is less than 250 micrometers, less than 200 micrometer, or less than 100 micrometers.

The contact between support pads 182 and sample holder 102 may produce hot spot on the holder when the thermal conductivity of the case or pad material is much higher than the thermal conductivity of the sealing fluid inside cavity 176 used to reduce evaporation of a biological test sample from through-holes 154. For example, the Fluorinert™ FC-70 material cited above has a thermal conductivity of 0.07 W·m$^{-1}$·K$^{-1}$, which is compared to a thermal conductivity of greater than 200 W·m$^{-1}$·K$^{-1}$ for common metals. In certain embodiments, the problem of hot spots is solved by configuring support pads 182 to have a total contact area with sample holder 102 that is low.

Figure 6:
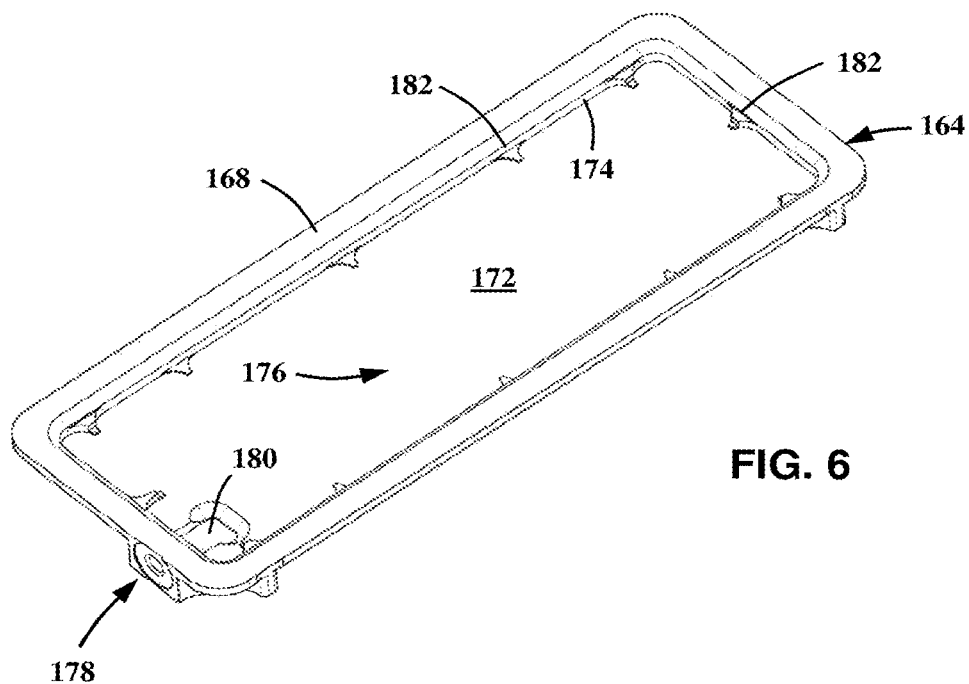
FIG. 6 is a perspective view the base shown in FIG. 4 without the sample holder.
Figure 7:
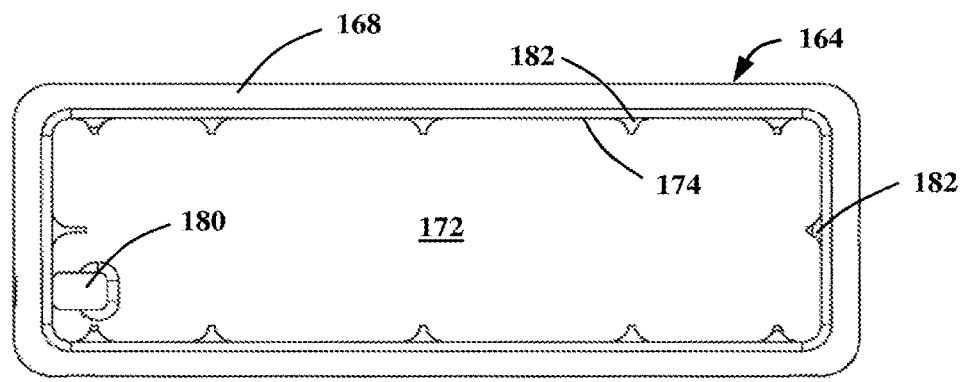
FIG. 7 is a top view of the base shown in FIG. 6.
Figure 8:
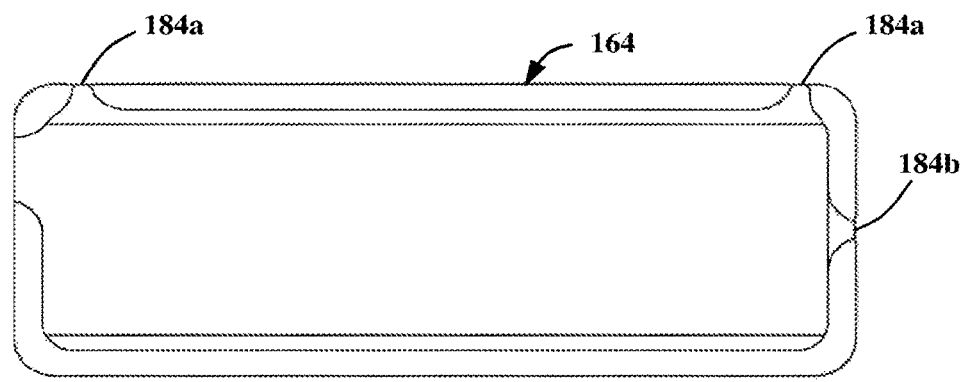
FIG. 8 is a bottom view of the base shown in FIG. 6.

A low total contact area may be achieve by providing a low number of support pads and by and by configuring individual pads to have a low contact area with sample holder 102. A lower bound on the number of support pads 182 is affected by the design constraint to maintain a low amount of bending or buckling of sample holder 102. In the illustrated embodiment, for example as seen in FIGS. 6 and 7, at least some of support pads 182 are tapered in a lateral direction; with a support pad 182 being relatively wide near side wall 174 and tapering off in width toward a tip of support pad 182. In this manner, the rigidity of support pads 182 is maintained, while the contact area with sample holder 102 is maintained at a low level that provide a low level of heat transfer into the hot spot.

In certain embodiments, sample holder 102 is secured or attached to base 164 prior to shipment to a customer, for example, to reduce or eliminate human contact with sample holder 102 during sample loading and use in system 100 by a customer or end user. In such embodiments, a tool or specialized fixture may be utilized so that a small amount of pad material is displaced laterally (e.g., along a plane parallel to bottom surface 172), where the laterally displaced material is in an amount sufficient secure, hold, or lock sample holder 102, but sufficiently small to eliminate bending or warping of sample holder 102. Alternatively, the amount of laterally displaced material is in an amount sufficient secure, hold, or lock sample holder 102 and to bend or warp sample holder 102 at or below a predetermined level.

In certain embodiments, an outer surface of base 164 comprise a plurality of registration features 184 to register and align case 150, sample holder 102, and/or through-holes 154 within system 100. For example, the two registration features 184a are used to align or register case 150 along an axis perpendicular to one of the long edges of sample holder 102, while registration feature 184b is used to align or register case 150 along an axis parallel to the long edges of sample holder 102.

Figure 9:
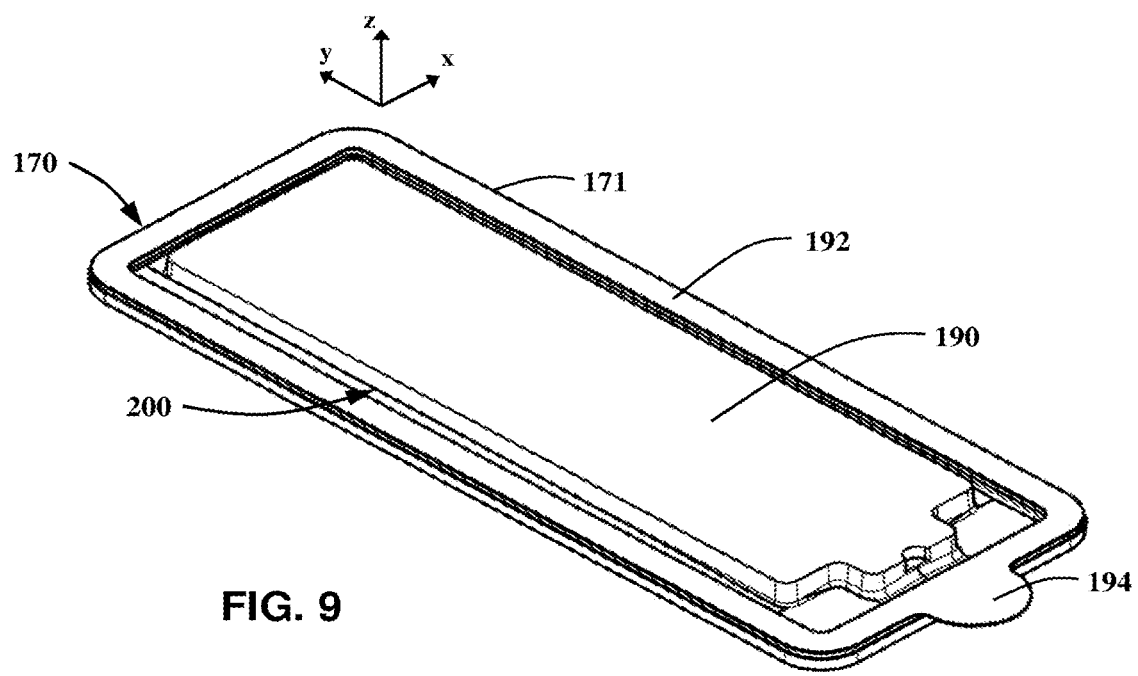
FIG. 9 is perspective view of the bottom of a cover according to an embodiment of the present invention.
Figure 10:
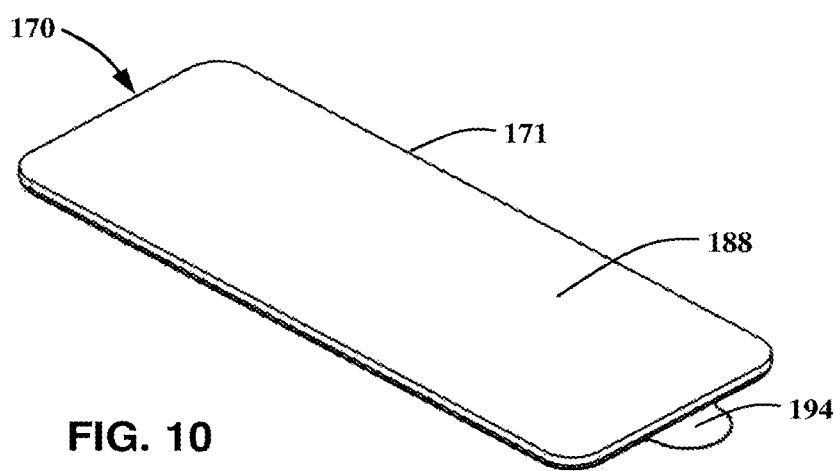
FIG. 10 is perspective view of the top of the cover shown in FIG. 9.

Referring to FIGS. 9-11, cover 170 comprises an outer surface 188 and an inner surface 190 including a rim 192 that interfaces with top surface 168 of base 164. At least portions of cover 170 comprise a transparent or relatively transparent in material to provide optical access to through-holes 154 and the biological or reference samples contained therein. Cover 170 may be made of a biocompatible material or another material if cover 170 is isolated from the biological samples contained in through-holes 154. Suitable materials for cover 170 include, but are not limited to, glass, acrylics, styrenes, polyethylenes, polycarbonates, and polyproplenes. In certain embodiments, the material comprises Cyclo Olefin Polymer (COP). In certain embodiments, cover 170 may include a lenslet array or diffractive optical element (not shown) configured to condition light being directed to or from through-holes 154. Cover 170 may be fabricated with seal 171 attached thereto. Alternatively, seal 171 is provided to a customer or user separate from cover 170, which are then attached to one another prior to use and application with base 164. Seal 171 may include an adhesive material on at least one surface for adhesion to base 164 and/or cover 170. Seal 170 may optionally include a removable non-stick layer 194 disposed over the adhesive material that is removed prior to use.

The samples contained in reaction regions 154 of sample holder 102 may be processed according to various methods, assays, or protocols. In certain embodiments, reaction regions 154 of sample holder 102 are thermocycled during a PCR assay or protocol. Thermocycling may be provided using thermal controller 108 and/or optical system 106 of instrument 100 to provide a qPCR, dPCR, or other end-point PCR assay or protocol. Additionally or alternatively, thermocycling may be provided using an external thermocycler, then subsequently viewed or analyzed using an optical reader such as optical system 106. During thermocycling of the samples contained in reaction regions 154 of sample holder 102, outgassing may occur in the sealing fluid contained within cavity 176 of case 150. In such cases, the outgassing may result in the formation of bubbles as the temperature of the sealing fluid increases, for example, during thermocycling over a temperature range from 60 degrees Celsius to 95 degrees Celsius or to 100 degrees Celsius.

In certain embodiments, inner surface 190 comprises a surface profile, shape, or contour 200 that controls or manages the formation of such bubbles in the sealing fluid contained in cavity 176 of sample holder 102. Such profiles take advantage of the natural tendency of bubbles to locate or move toward the top of a liquid media due to buoyancy. In certain embodiments, contour 200 and inner surface 190 comprise a central zone 210, peripheral zone 212, side zones 214, first end zone 220, and second end zone 222. Each zone may be further portioned. For example, in the illustrated embodiment shown in FIG. 11, first end zone 220 comprises a first area 230, a second area 232, and a third area 234. In discussing the shapes and locations of zones 210, 212, 214, 220, 222 and areas 230, 232, 234, a coordinate system will be adopted in which locations on inner surface 190 are more positive that locations on outer surface 188.

When assembled with the other components of case 150 and sample holder 102, central zone 210 is preferably suitable for optical inspection of, and located over, the plurality of through-holes 154 and any other features of sample holder 102 for which optical monitoring or inspection is desirable or required. For example, the central zone 210 may also extend over alphanumeric characters 160 and/or a barcode 162 so that they are available for optical inspection. Outer and inner surfaces 188, 190 within central zone 210 may be optically flat and parallel to one another. Alternatively, surfaces 188, 190 within central zone 210 may be optically flat and have a small offset angle relative to one another, for example, to reduce or eliminate multiple reflections between the surfaces, which reflections might reduce the image quality of data signals received by optical sensor 132. The offset angle between surfaces may be greater than or equal to 0.1 degrees and less than or equal to 0.5 degrees, 1 degree, 2 degrees, or 5 degrees, depending on the imaging specifications for system 100. In some embodiments, either or both surfaces 188, 190 may have an offset angle relative to a top surface of sample holder 102, for example an offset angle greater than or equal to 0.1 degrees and less than or equal to 0.5 degrees, 1 degree, 2 degrees, or 5 degrees, depending on the imaging specifications for system 100.

In the illustrated embodiment in FIG. 11, trough 250 has a bottom surface that is entirely below central zone 210 for the coordinate system shown in FIGS. 9 and 11B-11D, in which a positive direction along a normal to outer surface 188 (z-axis) is in a direction from outer surface 188 to inner surface 190. Thus, when case 150 is installed in system 100 with outer surface 188 above inner surface 190, any bubbles in cavity will tend to be located in trough 250 rather than in the area of central zone 210. In certain embodiments, trough 250 surrounds or encloses central zone 210 when viewed from below (e.g., as seen from the view in FIG. 11A); however, other configurations possible.

Figure 11A:
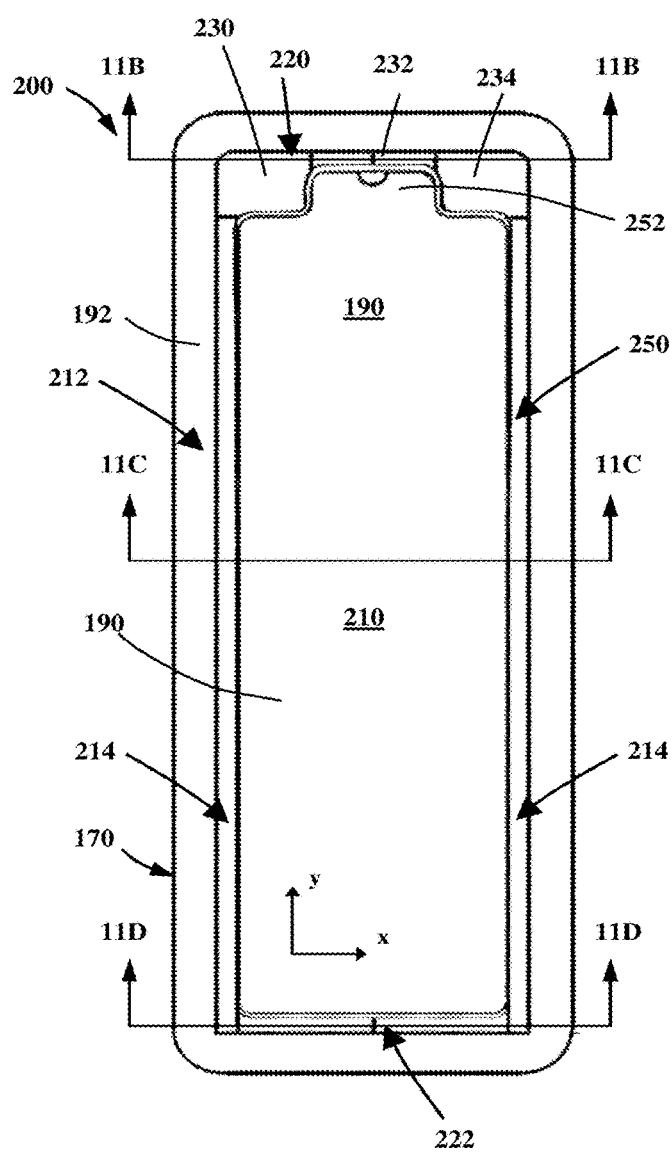
FIG. 11A is bottom view of cover shown in FIG. 9.

In certain embodiments, at least portions of central zone 210 are disposed at a minimum value, coordinate, or depth 240 and at least a portion of trough 250 is disposed at a maximum value, coordinate, or depth 242. In the illustrated embodiment, zones 212, 214, 222 form a channel, cannel, or trough 250. Trough 250 may have a constant depth along the entire trough. Alternatively, for example as shown in FIG. 11, trough 250 may have a bottom surface profile that varies in depth. For example, areas 230 and 234 of zone 220 have a depth equal to the minimum depth 240, while the remaining zones and areas of trough 250 have a depth that is less than the minimum depth. In such embodiments, any gas or bubbles in cavity 176 will tend to be located in areas 230, 234 in preference to the other zones of inner surface 190. As seen in FIG. 11A, end zone 220 may also be generally wider than other portions of trough 250 to further provide an enlarged area for the collection of bubbles or gas within the sealing fluid filling cavity 176, for example, to prevent first end zone 220 from filling with gas or bubbles, which could then spill over into unwanted portions of inner surface 190. In addition, enlargement of first end zone 220 may be advantageously configured maintain a relatively small overall size of case 150 while also providing a volume that is large enough to collect anticipated volumes of bubbles or entrapped gas. To aid in keeping the size of case 150 relatively small, central zone 210 includes a tabbed portion 252 that provides quality optical access to alphanumeric characters 160, which does not extend over the entire width of sample holder 102. Thus, areas 230, 234 of first end zone 220 have the enlarged width or volume compared to other portions of trough 250, while the width of area 232 is smaller and may be equal to or about equal to the width of other portions of trough 250.

Figure 11B:
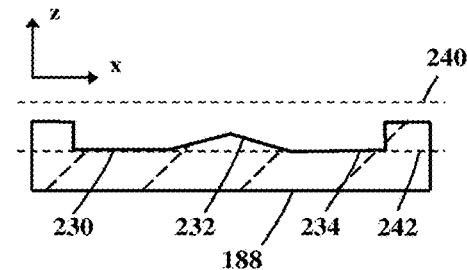
FIGS. 11B-11D are cross-sectional views of portions of the cover shown in FIG. 11A.
Figure 11C:
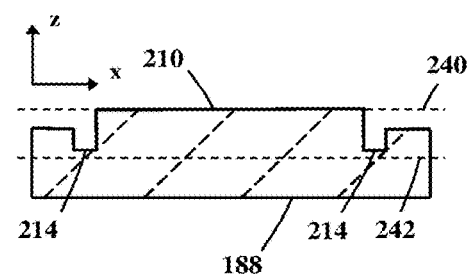
Figure 11D:
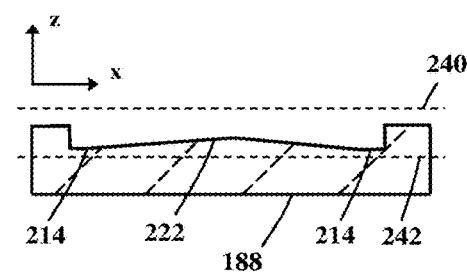

In certain embodiments, first end zone 220 may have a constant depth or substantially constant depth over its entire length. Alternatively, as in the illustrated embodiment shown in FIGS. 11A and 11B, areas 230, 234 of first end zone 220 may be separated by area 232, where area 232 has a depth that is less that either areas 230, 234. Areas 230, 234 may have the same depth or one of areas 230, 234 may have a depth that is less than the other; however, in such embodiments, area 232 has a depth that is less than the depth of areas 230, 234. The depth of area 232 may be constant or variable. For example, area 232 may have a profile that is sloped toward one of areas 230, 234 or is sloped toward both areas 230, 234, as illustrated in FIG. 11B. Second end zone 222 may have a constant depth or have a depth that is varied or sloped toward one of the side zones 214. Alternatively, second end zone may profile that is sloped toward both side zones 234, as illustrated in FIG. 11D. Both side zones 214 may have the same or different depth profiles compared to one another. In the illustrated embodiment, the depth of side zones 214 both less than the maximum depth of first end zone 220. All or a portion of each side zone 214 may have a depth that varies or slope along the channel formed thereby. For example, one or both side zones may be sloped from a minimum depth value at or near second end zone 222 and that increases to a maximum depth at or near first end zone 220.

Under some circumstances, the formation of bubbles in the sealing fluid contained within cavity 176 of case 150 can occur during thermocycling at one or more nucleation sites located along bottom surface 172 of case 150, for instance, during a PCR, qPCR, or dPCR procedure, assay, or protocol. For example, during thermocycling, system 100 may be configured to transfer heat between a thermal controller and case 150 through bottom surface 172 of case 150. Under such circumstances, bubbles may grow in size from a nucleation site as the temperature of the surface is increased during thermocycling. The bubble can grow to such an extent that it contact the bottom surface of sample holder 102 and produce a pressure against the bottom of one or more of the reaction regions or through-holes 154. It has been discovered that the gas pressure against the bottom of a reaction region or through-hole 154 may be sufficient to push some or all of the sample fluid contained in the reaction region or through-hole 154 out of the top of the pressurized reaction region or through-hole. It has been further discovered that sample fluid pushed out of the pressurized through-holes can be transferred or "bridge" over the top surface of sample holder 102 to one or more adjacent reaction regions or through-holes 154. This transfer of sample fluid may result in contamination of the sample solution in the adjacent reaction region or through-hole 154. The discovery of this problem has led implementation of various structures and method for mitigating or eliminating this source of sample fluid contamination. As used herein, the term "bridge" means to move liquid sample from one reaction region, well, or through-hole of a sample holder to another reaction region, well, or through-hole of the sample holder.

In certain embodiments, the bottom surface 172 of case 150 may be polished, coated, and/or otherwise treated to reduce or eliminate the transfer of sample fluid between adjacent reaction regions 154, for example, by eliminating or reducing the production or occurrence of bubbles along bottom surface 172 of case 150. In some embodiments, such a treatment of bottom surface 172 provides a surface roughness that is below a predetermined value. By maintaining the surface roughness below the predetermined value, the occurrence of nucleation sites along bottom surface 172 may be reduced or eliminated, thus reducing or eliminating the occurrence of bubbles along bottom surface 172 and/or reducing the size of such bubbles to an extent that preclude contact or pressurization of reaction regions or through-holes 154. In other embodiments, the spacing between bottom surface 172 of case 150 and the bottom surface of sample holder 102 may be selected to reduce the size of the bubbles formed along bottom surface 172 and/or to preclude or reduce contact or pressurization of reaction regions or through-holes 154.

Figure 12A:
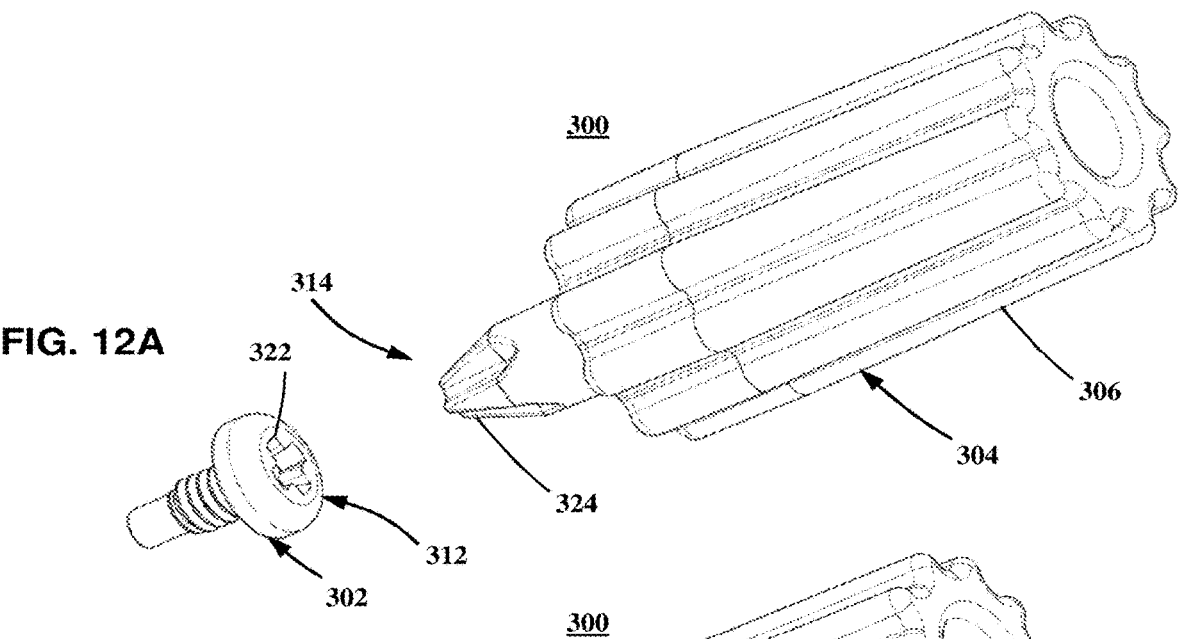
FIGS. 12A-12C are perspective views of a plug assembly according to an embodiment of the present invention.
Figure 12B:
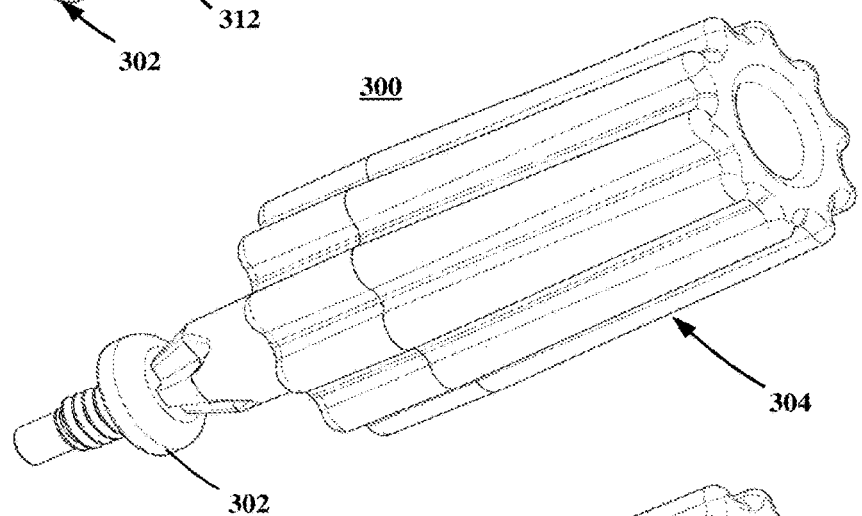

In certain embodiments, it has been discovered that the angle from a horizontal plane of sample holder 102, bottom surface 172, and/or case 150 may be selected to prevent or reduce the transfer of sample solution between reaction regions or through-holes 154. As used herein, the term "horizontal" means parallel to the horizon of the planet earth. In such embodiments, the buoyancy of bubble within the sealing fluid contained within cavity 176 of case 150 caused bubbles located along or near bottom surface 172 to move from an initial location or nucleation site. The movement may cause one or more bubbles to toward one end of case 150 or cavity 176 and/or into a region thereof that not below any of the reaction regions or through-holes 154. Thus, the use of bubble buoyancy within a fluid produces the unexpected result of reducing or eliminating the transfer or bridging of sample solution between reaction regions or through-holes 154, which in turn reduces or eliminates cross-contamination sample solution between reaction regions or through-holes 154. Referring to FIGS. 12 and 13, in certain embodiment, case 150 includes a plug assembly 300 comprising a plug 302 and a plug driver 304 detachably coupled or joined to plug 302. Plug driver 304 is used to apply a driving force or torque to plug 302 as a means for sealing or plugging fill port 178 of case 150. As a means of providing a more compact unit, it is desirable in certain embodiments to separate plug driver 304 from plug 302 after insertion into fill port 178. To facilitate application of the driving force or torque, plug driver 304 may comprise a gnarled proximal end 306, for example, to allow direct hand application of the driving force or torque. Additionally or alternatively, the proximal end of plug driver 304 may comprise a configuration that allows tool or fixture to be applied for providing the desired driving force or torque.

Figure 12C:
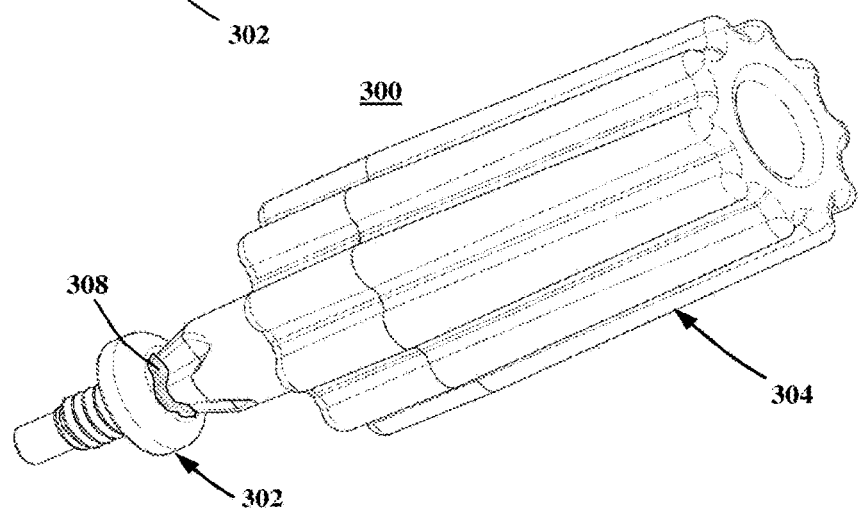
Figure 13:
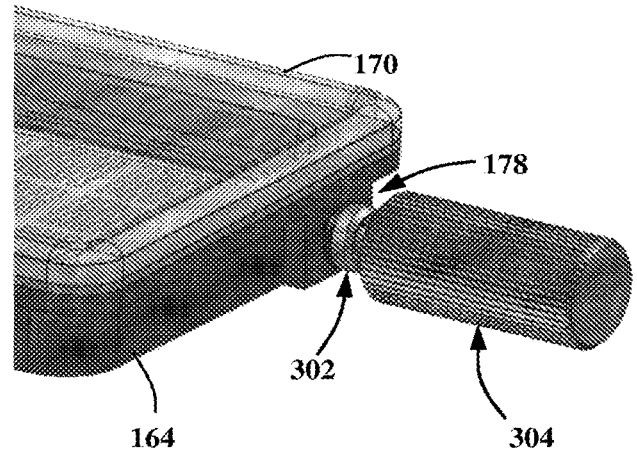
FIG. 13 is a perspective view a case according to an embodiment of the present invention showing attachment of the plug assembly shown in FIG. 12C.

Plug driver 304 may be coupled or attached to plug 302 using an epoxy 308, as illustrated in FIG. 12C. Alternatively, coupling or attachment of plug driver 304 to plug 302 may be providing using a glue or other type of adhesive, a solder joint, a weld joint, or the like. Plug 302 comprises a proximal end 312 having a first pattern 322, while plug driver 304 comprise a distal end 314 having a second pattern or form 324. First and second patterns 322, 324 complement one another in a way allow the patterns to be joined in a way allowing a force or torque to applied to plug driver 304 for driving plug 302 in order to plug or seal fill port 178 of case 150. In the illustrated embodiment, first pattern 322 has the form of a Phillips head screw, while second pattern 324 has the form of the tip portion of a Phillips head screw driver. Alternatively, first pattern 322 may have the form of the tip portion of a Phillips head screwdriver, while second pattern 324 may have the form of a Phillips head screw. Other types of standard bolt or screw head patterns may alternatively be used including, but not limited to, slot, socket, hex socket, hex head, one way screw head, spanner head, Trox, and the like. Alternatively, patterns 322, 324 may be a custom pattern and its complement.

In certain embodiments, the joint between plug driver 304 and plug 302 is sufficiently strong that a driving force or torque may be applied to plug driver 304 that is sufficient to plug or seal fill port 178 of case 150. Generally, the joint between plug driver 304 and plug 302 is sufficiently strong that the driving force or torque does not break or does not damage the joint and/or patterns 322, 324. In addition to these characteristics, the joint between driver 304 and plug 302 is sufficiently weak so that separating or breaking force or torque may be applied that breaks, separates, or decouples the joint between plug driver 304 and plug 302 in a manner that does not disturb or damage the seal produced at fill port 178 using the driving force or torque. In certain embodiments, the separating force or torque is only a little greater that the driving force or torque. For example, the separating force or torque may be less than or equal to 120% of the driving force or torque, less than or equal to 150% of the driving force or torque, less than or equal to 200% of the driving force or torque, or less than or equal to 400% of the driving force or torque. In certain embodiments, the separating force or torque is of a different type, or in a different direction, than the driving force or torque. For example, in the illustrated embodiment, plug 302 includes a threaded distal end that is screwed into fill port 178 using a driving torque about an elongate axis passing through both plug 302 and plug driver 304. Once plug 302 has been secured into fill port 178, a separating torque may be applied about a different axis, for example about an axis that is normal to the elongate axis. Alternatively or additionally, a lateral force perpendicular to the elongate axis may be applied to plug driver 304 as a separating force.

Figure 14:
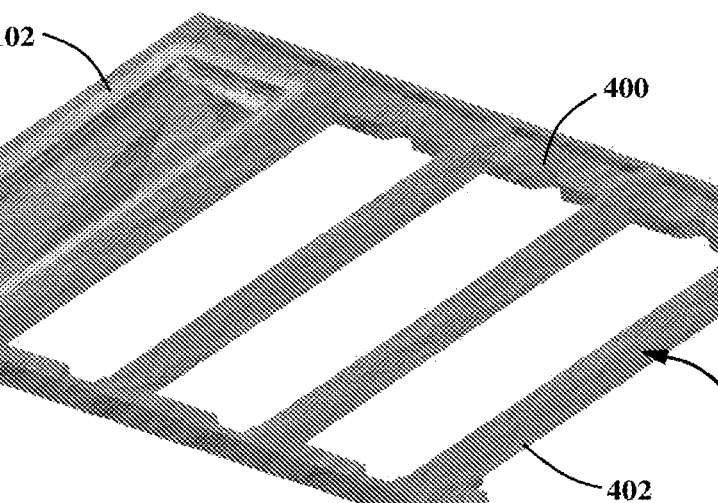
FIG. 14 is a perspective view of the top of a carrier according to an embodiment of the present invention and containing the case shown in FIG. 5
Figure 15:
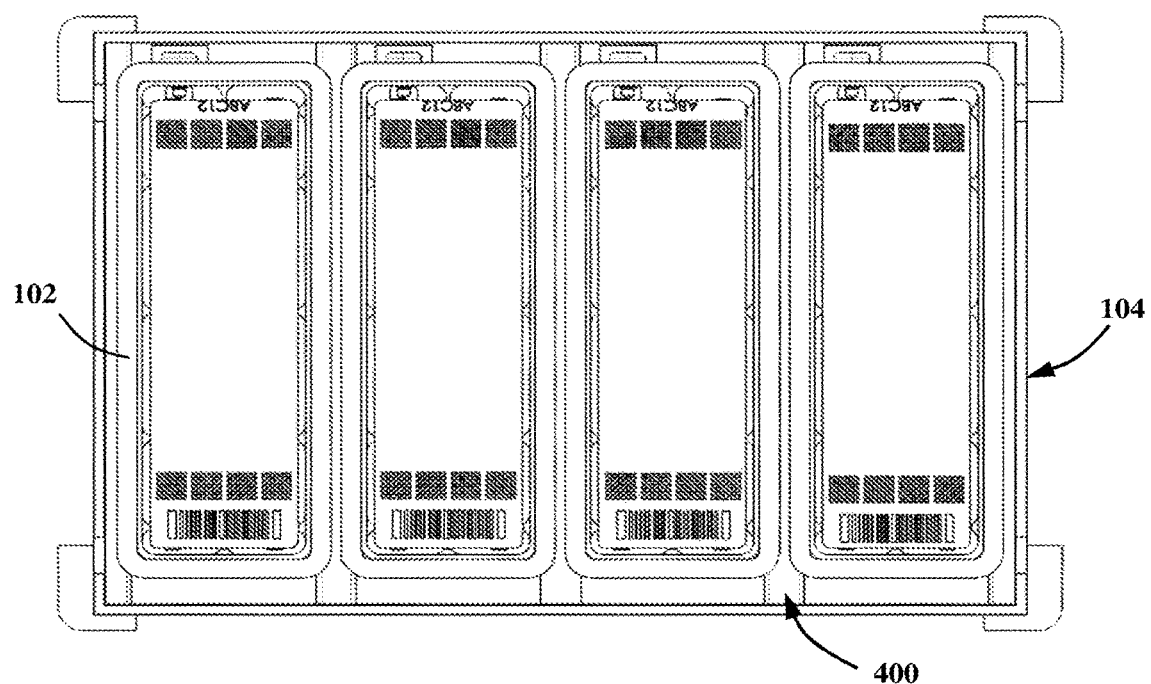
FIG. 15 is top view of the carrier shown in FIG. 14 and containing four of the bases and sample holders shown in FIG. 4.

Referring to FIGS. 14-15, carrier 104 may be configured support or hold a plurality of sample holders 102, for example, the four sample holders 102 shown in FIG. 15. Carrier 104 comprises a proximal or top side 400 that is configured to accommodate each of four separate sample holders 102 and a distal or bottom side 402 that is configured to interface or engage thermal controller 108 and/or configured to interface or engage each sample holder 102 with engage thermal controller 108. System 100 may be configured to accommodate one, two, three, or four sample holders using the same carrier in each case. For example, system 100 may include one or more sensors configured to sense how many sample holders 102 are present on or in carrier 104, and then make appropriate adjustment to test protocols for processing the biological samples, optical system configuration or performance, image processing algorithms, data presentation algorithms, and/or other mechanical, electrical, thermal, or optical elements or subsystems of system 100.

In certain embodiments, system 100 includes a one or more carrier configured to hold more or less than four sample holders 102. In other embodiments, system 100 includes one or more additional carriers configured to hold other types of sample holders. For example, system 100 may include additional sample holders configured to accommodate formats to hold 48, 96, and/or 384 individual samples. In such embodiments, a different carrier may be provided for each sample holder format, wherein each carrier comprise a first portion (e.g., a bottom side) that is the same or nearly the same as that of carrier 104, but wherein each carrier also comprises a second portion (e.g., a top side) having a different construction to accommodate each of the different types of sample holders.

Figure 16:
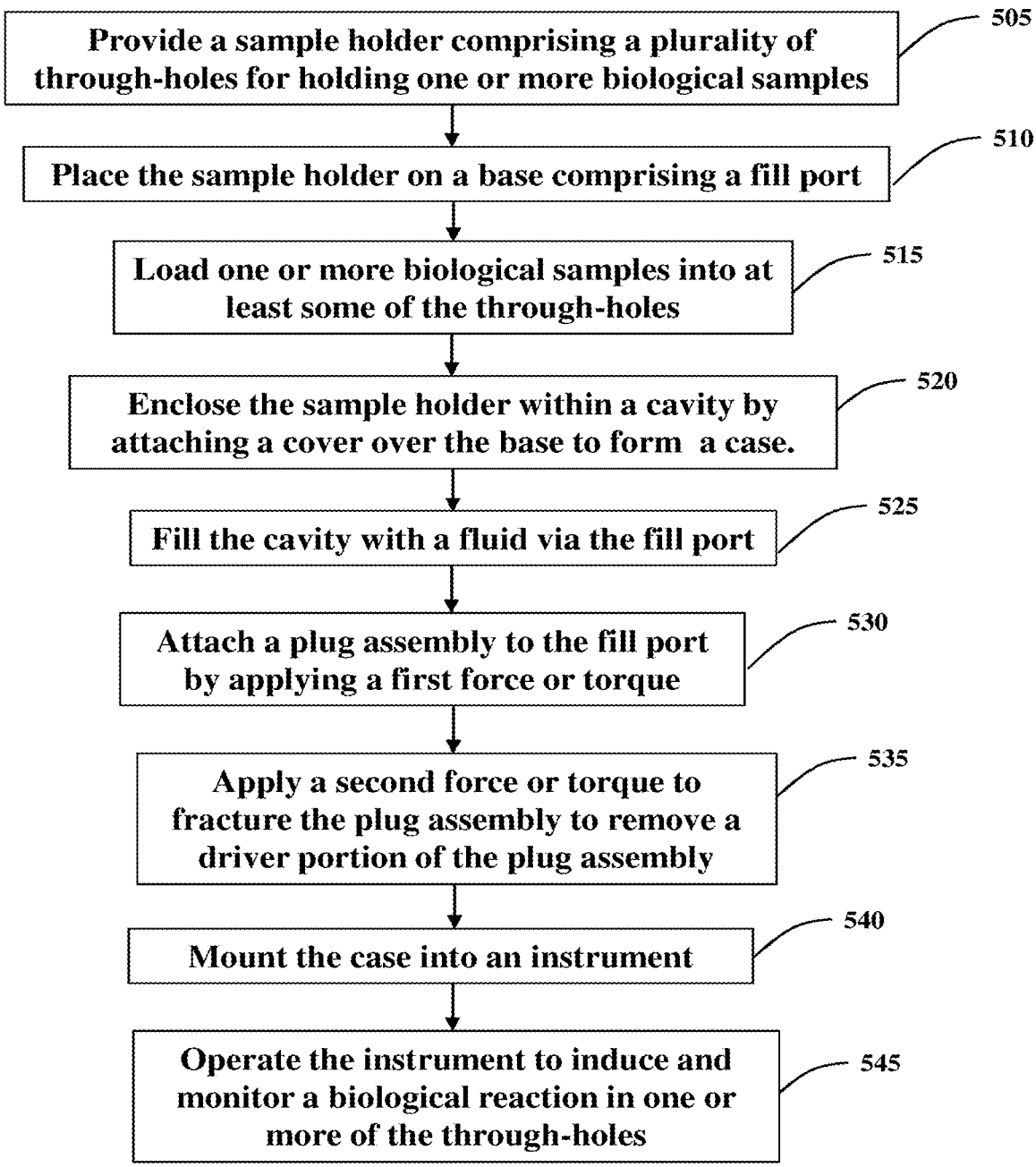
FIG. 16 is a flow chart of a method according to the present invention.

Referring to FIG. 16, in certain embodiments, a method 500 includes an element 505 comprising providing sample holder 102. Method 500 also includes an element 510 comprising locating, placing, or mounting sample holder 102 on or within base 164. Method 500 further includes an element 515 comprising loading one or more biological samples into at least some of through-holes 154. Method 500 additionally includes an element 520 comprising enclosing sample holder 102 within cavity 176 by attaching cover 170 onto or over base 164. Method 500 also includes an element 525 comprising filling cavity 176 with a fluid via fill port 178. Method 500 further includes an element 530 comprising attaching plug assembly 300 to the fill port 178 by applying a first force or torque. Method 500 additionally includes an element 535 comprising applying a second force or torque to fracture, part, or break plug assembly 300 and thereafter removing plug driver 304 from plug assembly 300. Method 500 also includes an element 540 comprising mounting case 150—including base 164, sample holder 102, and cover 170—into instrument 100. Method 500 further includes an element 545 comprising operating the instrument to induce and monitor a biological reaction in one or more of through-holes 154.

Regarding element 510 of method 500, sample holder 102 may be located on support pads 182 such that a bottom surface 172 of sample holder 102 is parallel or substantially parallel to bottom surface 172 of base 164. At least some of the support pads 182 may comprise a proximal portion having a top surface and attached to and/or integral with one of the side walls 174, and a distal portion forming a step with a top surface that is disposed closer to bottom surface 172 than the top surface of the proximal portion. The width of the distal portion may be less than that of the proximal portion, for example, to reduce the amount of physical contact between sample holder 102 and support pad 182. On such support pads, sample holder 102 sits on the distal step portion of support pad 182 and may either touch a side wall of the proximal pad portion or have a gap between it and the proximal pad portion. In the later case, tool may be used to laterally displace some of the material of the proximal pad portion to provide a holding force between the proximal pad portion and sample holder 102. Additionally or alternatively, sample holder 102 may be placed on support pads 182 that are configured to only contact the bottom side of sample holder 102, for example, to help reduce or prevent bending or bulking of the front and back faces of sample holder 102 (i.e., the faces into which through-holes 154 are located). In certain embodiments, an adhesive may be used on some or all the support pads 182 to secure sample holder 102 to base 164. In yet other embodiments, a downward force on the upper face of sample holder 102 is used to secure sample holder 102 to base 164, for example, at downward force on the sample holder 102 in the vicinity of at least some of the support pads 182. For example, a downward force may be applied to a peripheral portion of sample holder 102 by cover 170 when attached at element 520 of method 500. The downward force may be applied directly to sample holder 102 or through an intermediate spacer, seal, or gasket that is located on top of sample holder 102, for example, locate over a peripheral portion of sample holder 102. In some embodiments, samples are loaded into at least some of through-holes 154 prior to locating the sample holder 102 on or within base 164.

Regarding element 515 of method 500, biological samples may be loaded into one or more of through-holes 154 using one or more conventional pipettes. Alternatively, a custom loader may be used, for example, a loader comprising a plurality of pipette tips that allow more than one of through-holes 154 to be loaded simultaneously. In certain embodiments, the loader may comprises the loader disclosed in U.S. patent application Ser. No. 13/170,563, which is herein incorporated by reference in its entirety as if fully set forth herein. The biological samples may include one or more nucleotide sequences, amino acid sequences, or other biological macromolecules including, but not limited to, oligonucleotides, genes, DNA sequences, RNA sequences, polypeptides, proteins, enzymes, or the like. In addition, biological samples may include other molecules for controlling or monitoring a biological reaction including, but not limited to, primers, hybridization probes, reporter probes, quencher molecules, molecular beacons, fluorescent dyes, chemical buffers, enzymes, detergents, or the like. Additionally or alternatively, biological samples may include one or more genomes, cells, cellular nucleuses, or the like.

Regarding element 520 of method 500, cover 170 may be attached to base 164 about a peripheral region of base 164, for example, along top surface 168 of base 164. An adhesive may be used to attach cover 170 directly to base 164. Alternatively, gasket 171 may be used to attach cover 170, where an adhesive has been applied to top and bottom surface of gasket 171 and/or to portions of mating surfaces on base 164 and/or cover 170. The adhesive may be applied by a user just prior to attachment of cover 170 or may be applied during fabrication of cover 170, base 164, and/or gasket 171. In certain embodiments, a removable non-stick layer is applied on top of an adhesive layer that is removed prior to attachment of cover 170, for example, removable non-stick layer 194 shown in FIGS. 3, 9, and 10 over seal 171.

Regarding elements 525, 530, and 535 of method 500, a pipette, needle, or similar filling device may be inserted into fill port 178. A tip of the filling device inserted into the vicinity of indentation 180 in bottom surface 172 of base 164, for example, so that liquid may enter from into indentation 180 and air leave through insertion port 178 behind the filling device tip. Alternatively, a separate vent port may be provided in base 164 or cover 170 to allow air in cavity 176 of case 150 to leave from a different or addition location from fill port 178. In such embodiment, the filling device may be configured to form a seal with insertion port 178. Once cavity 176 has been filled or nearly filled with sealing fluid or liquid, the filling device may be removed or extracted from fill port 178, after which fill port 178 and/or any existing vent port may plugged or sealed in order to isolate the filled cavity 176 from the outside environment and/or to prevent or impede air from entering, or liquid from leaving, cavity 176. Fill port may be sealed using plug assembly 300, as described above herein. Alternatively, any type of plug or seal known in the art may be used. In certain embodiments, fill port 178, includes a valve that allows the filling device to be inserted during filling and then automatically closes as seals fill port 178 upon extraction of the filling device. In addition, if any separate vent ports are incorporated, these also may have a valve, such as a check valve, to maintain a closed cavity 176 after filling. In some embodiments, fill port 178 comprises a self-healing diaphragm that may be punctured by the filling device (e.g., a syringe needle) and then remain sealed upon removal of the filling device.

Regarding elements 540 and 545 of method 500, instrument 100 is configured to receive case 150—which includes sample holder 102 and its biological samples. In certain embodiments, one or more cases 150 are mounted on or in carrier 104, after which carrier 104 is received by instrument 100, along with the one or more cases 150. Instrument 100 is then used to perform one or more biological processes or experiments on the biological samples contained within through-holes 154. Instrument 100 may be configured to a qPCR, dPCR, end-point PCR, sequencing, genotyping, or other such procedure on one or more of the samples contained in through-holes 154 of sample holder 102. In certain embodiments, one or more sample holders 102 and/or cases 150 may be processed simultaneously by instrument 100 or associated optical system 106. As discussed above herein, one or more cases 150 may be mounted or attached to carrier 104, which is then received by instrument 100. In addition, instrument 100 may be configured to also receive other types of sample formats including, but not limited to, microtiter plates containing 48 sample wells, 96 sample wells, and 384 sample wells.

Referring to FIGS. 17-21, in certain embodiments an enclosure, housing, or case 600 comprises a base 602 and a cover or lid 604 configured to sealably engage base 602. Base 602 and cover 604 may be joined together to form a cavity or chamber 608, which may receive or contain a sample holder, substrate, planar member, or plate 610. Sample holder 610 may be part of base 602, or may be separate and/or distinct from base 602 and be configured to be mounted or held by base 602. Case 600 may further comprise an adhesive, seal, or gasket 612 disposed between base 602 and cover 604, for example, to seal or isolate cavity 608 and sample holder 610 from an outside environment.

In certain embodiments, sample holder 610 is attached or joined with base 602. Sample holder 610 may be attached or joined during fabrication or assembly of base 602 by a manufacturer. In other embodiments, sample holder 610 is attached or joined to base 602 by a user, for example, after sample holder 610 has been loaded with sample or solution containing a biological substance. Alternatively, sample holder 610 is attached to the base prior to loading of a sample or solution containing a biological substance. In either of these embodiments, sample holder 610 may be introduced into sample holder 610 using a loading mechanism or system configured to receive sample holder 610 and/or base 602. For example, a loading mechanism like that disclosed in U.S. patent application Nos. 61/612,008 or 61/723,658 may be used to load sample holder 610 with one or more biological samples.

Figure 17:
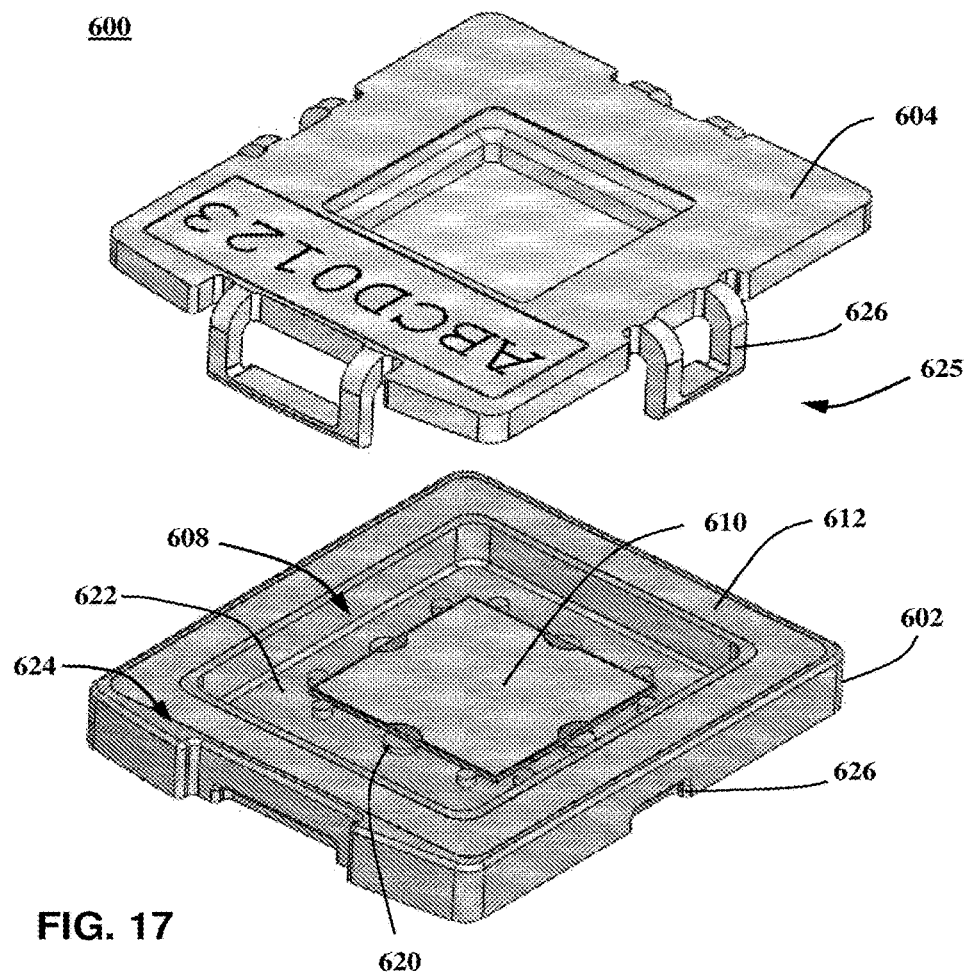
FIG. 17 is an exploded, perspective view of a case according to another embodiment of the present invention.
Figure 18:
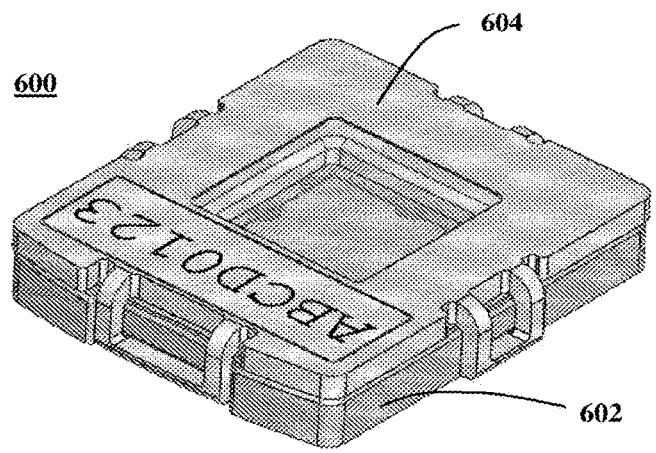
FIG. 18 is perspective view of the case shown in FIG. 17.
Figure 19:
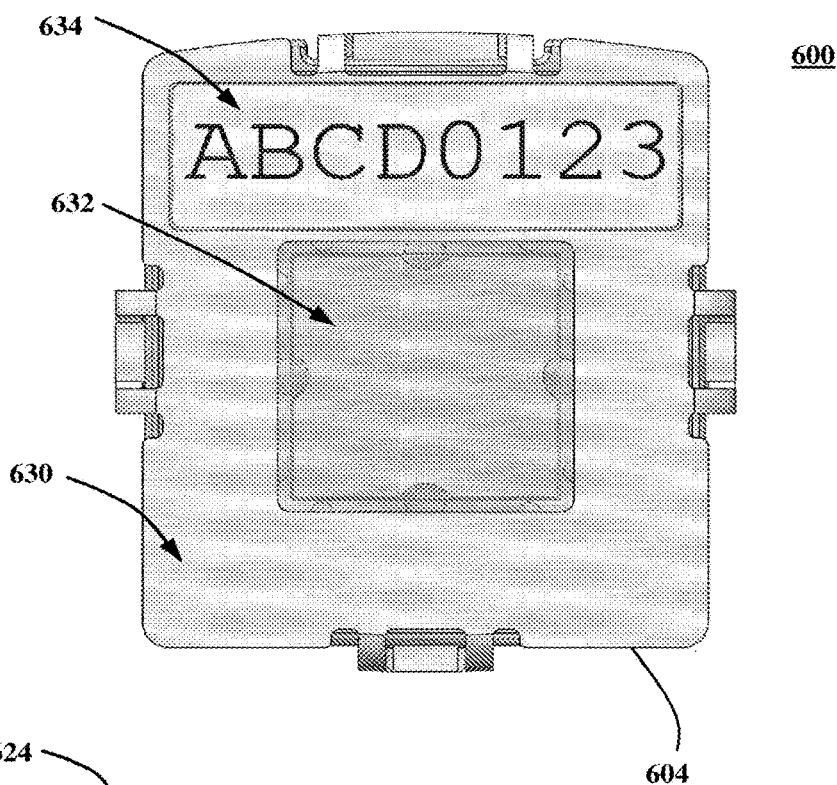
FIG. 19 is a front view of the case shown in FIG. 17.
Figure 20:
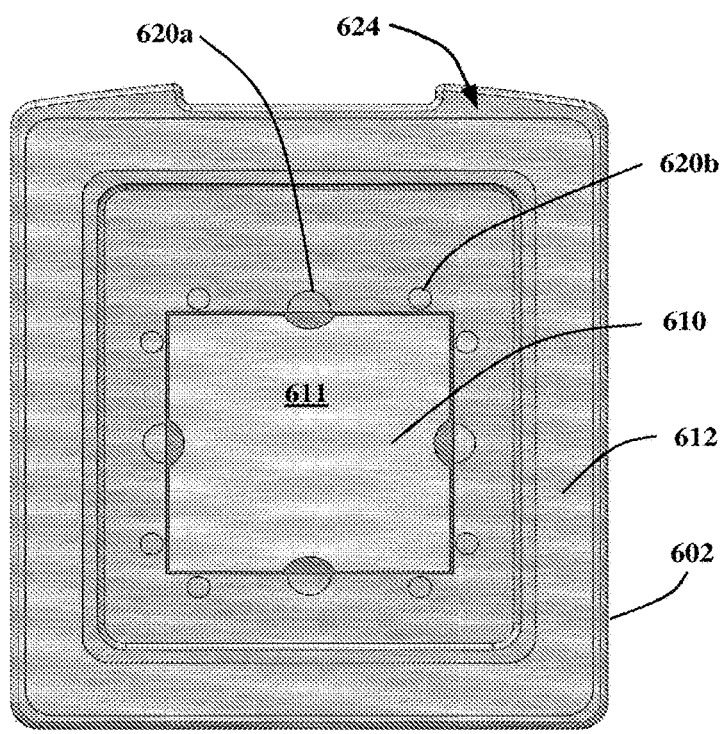
FIG. 20 is a front view of a base of the case shown in FIG. 17 showing a sample plate attached to the base.

Referring to FIGS. 17 and 20, base 602 may comprise a plurality of bosses, tabs, staking sites, and/or support pads 620 (e.g., tabs 620a and 620b in the illustrated embodiment) that are configured to hold and/or locate sample holder 610 within base 602 and cavity 608. Tabs 620 may be configured with one or more of the features discussed above with regard to tabs 182. For example one or more tabs 182 may be staked so that material from the tab is deformed or moved to hold sample holder 610 firmly within base 602. Additionally or alternatively, sample holder 610 may be glued to one or more tabs 182 using an adhesive, epoxy, or glue. In certain embodiments, gluing is used in conjunction with a glass or silicon sample holder 610 in order to avoid possible cracking or damage to such holder materials, which might be induced by use of a crimping or holding force produced by tabs 620.

Figure 21:
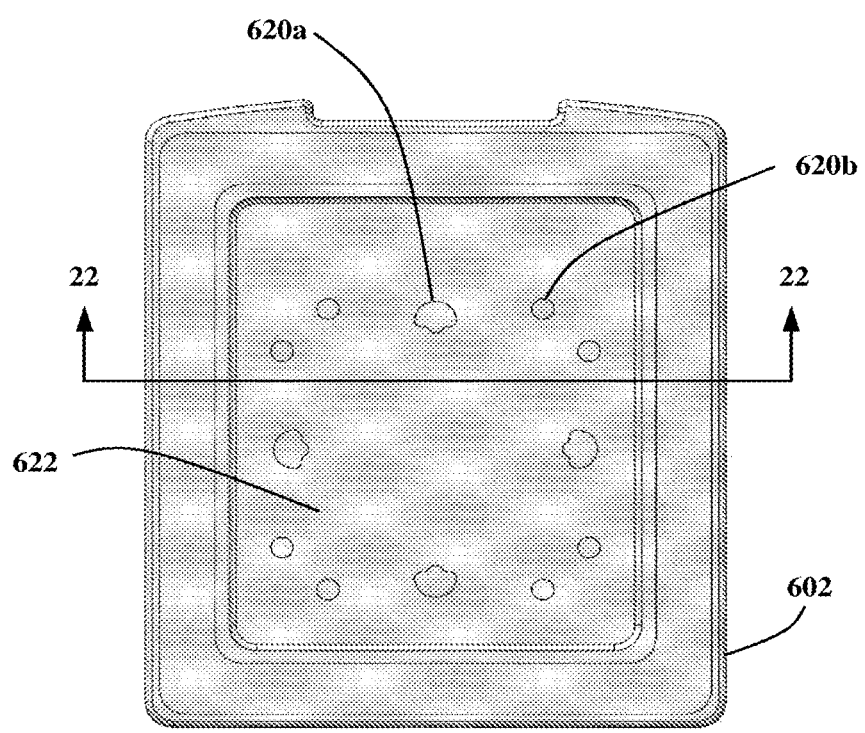
FIG. 21 is a front view of the base shown in FIG. 20 without the sample plate.
Figure 22:
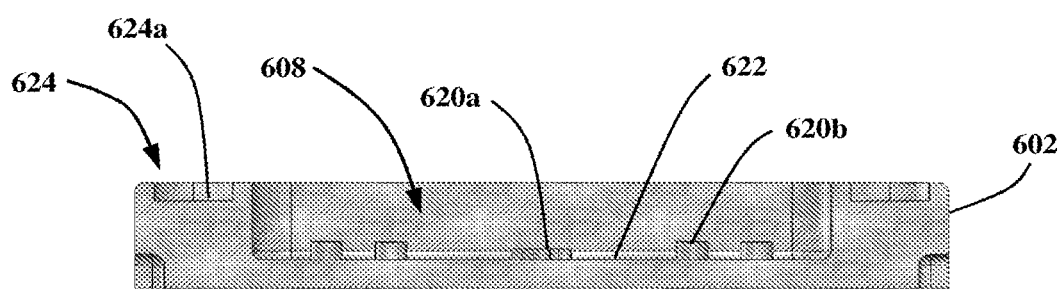
FIG. 22 is a cross-sectional view of the base shown in FIG. 21.

Referring to FIGS. 20-22, base 602 may comprise two sets of tabs 602a and 602b, each set of tabs having a different geometry from the other set. In the illustrated embodiment, tabs 620b are longer than tabs 620a by an amount sufficient to provide that some or all of the edges of sample holder 610 are engaged or held by tabs 620b when a face of sample holder 610 rests or sits on top of tabs 620a. The height of tabs 620a may be selected to hold or maintain sample holder 610 at a predetermined height above an inner bottom face 622 of base 602. In addition, the height of tabs 620a and the thickness of sample plate 210 may be selected to hold or maintain sample holder 610 at a predetermined distance below an upper inner face of cover 604. The gaps so produced between sample holder 610 and base 602, and between sample holder 610 and cover 604 may be selected to provide a predetermined thermal isolation and/or uniformity of sample holder 610 and/or the solutions or sample held therein.

Each of tabs 620a may be located at or near the center of some or all of the edges of sample holder 610. Each of tabs 620b may be located at or near some or all of the corners of sample holder 610. Alternatively, two or more tabs 620a may be located along one or more edges of sample holder 610, for example, to provide added support of sample holder 610, reduced thermal non-uniformity along sample holder 610, and/or reduced deformation of sample holder 610.

In the illustrated embodiment the shape of tabs 620a is configured to allow sufficient enough area to place a drop of glue or adhesive on the back side, while maintaining a relatively small contact area between sample holder 610 and tab 620a, thus reducing heat transfer between sample holder 610 and base 602. In addition, the shape of tabs 620a may be configured to reduce the amount of active area on sample holder 610 contacted by tab 620a, which might otherwise negatively reduce the number of reaction sites or regions on sample holder 610 that may be used to hold a sample.

An adhesive or glue may be applied to some or all of tabs 620a or tabs 620b, or a combination of some or all of tabs 620a and 620b. Additionally or alternatively, one or more of tabs 620b may be crimped, deformed, bent, or moved in order to apply a holding force to one or more edges of sample holders 610.

Referring again to FIGS. 17 and 20, base 602 may be configured to receive seal 612, for example, in the form of a gasket or adhesive configured to seal cavity 608. In certain embodiments, seal 612 provide a fluid-tight seal (e.g., airtight or liquid-tight seal) of cavity 608. For example, seal 612 may be configured to provide a fluid tight seal such that a liquid, such as Fluorinert, inside cavity 608 does not leak out during use (e.g., during thermal cycling of the sample in sample holder 610 in a PCR experiment or process). In the illustrated embodiment, base 602 comprises a face 624 configured to receive seal 612. As shown in FIG. 22, face 624 may include an inset groove or channel 624a configured to contain seal 612.

Referring again to FIGS. 17-19, cover 604 comprises an inner face (not visible in the figures) configured to engage or interface with face 624 of base 602. To aid in providing a seal between base 602 and cover 604, case 600 further comprises a clamping mechanism 625. In the illustrated embodiment, latch or clamping mechanism 625 comprises a plurality of clamps or clips 626 disposed on cover 604 and a plurality of corresponding indent or groove 628 configured to receive clips 626 so as to produce a seal between the mating parts. The plurality of clips 626 and indents 628 may be disposed along two or more edges of base 602 and cover 604. In the illustrated embodiment, the plurality of clips 626 and indents 628 may be disposed along all four edges of base 602 and cover 604. In certain embodiments, cover 604 comprises one or more clips 626 and base 602 comprises one more corresponding indents 628. In certain embodiments, clamping mechanism 625 is configured to provide a permanent or secure connection of cover 604 to base 602 so as to isolate the sample contained in sample holder 610 from the ambient environment, for example, to reduce or eliminate the release of high-copy DNA amplicons into a surrounding lab environment produced by a PCR or similar amplification process, thus reducing or minimizing environmental exposure to contaminants.

Referring again to FIG. 19, cover 604 comprises a peripheral portion 630, a central portion 632, and the plurality of clips 626 disposed about the edges of peripheral portion 630. Cover 604 may further comprise a label area 634 configured to receive a separate label containing alphanumeric characters, barcode, QR code (quick response code), or other type of marks or indicia. Alternatively, label area 634 is configured to directly receive alphanumeric characters, barcode, QR code, or other type of marks or indicia. Additionally or alternatively, label area 634 may comprise an RFID tag, holographic tag, diffraction grating, or other means for recording information on or in a surface, volume, or tag. Information included in label area 634 may include, but is not limited to, information regarding case 600 (e.g., instrument compatibility, geometric size or configuration, material properties, or the like), sample holder 610 (e.g., reaction regions size, density, geometric configuration, material properties, or the like), samples and/or reagents contained in sample holder 610, or the like.

Central portion 632 may be clear or transparent in order to provide optical access to sample holder 610. Inner and outer faces of central portion 632 may be of optical quality finish (flatness and surface roughness) it order to provide low aberration images of sample holder 610 and/or of the samples contained therein. Peripheral portion 630 may also be transparent or semi-transparent; however, the optical quality of the inner and/or outer surfaces of peripheral portion 630 may be lower than that of central portion 632. Instead of transparent, peripheral portion 630 may comprise a material or surface that is frosted, translucent, or opaque over all or a portion of its area.

In certain embodiments, central portion 632 comprises a separate window or part that may optionally be made of a different material than peripheral portion 630. In such embodiments, peripheral portion is configured with a mating aperture configured to receive window 632. Peripheral portion may include shelf or step disposed about one or more edges, and configured to provide an inlay for receiving window 632. A glue, adhesive, and/or sealant may be applied to mating surface between window 632 and peripheral portion 630 of cover 604, for example, to seal or isolate cavity 608 and sample holder 610 from an outside environment.

In other embodiments, central portion 632 and peripheral portion 630 may have a unitary construction and/or may comprise a single material. In such embodiments, central portion 632 may be molded, machined, polished, or otherwise processed in a different manner or way than peripheral portion 630. For example, peripheral and central portions 630, 632 may be cast from a common mode, wherein the mold surface has a different texture, structure, or roughness in mold regions corresponding to central portion 632 of cover 604 than in mold regions corresponding to peripheral portion 630 of cover 604. Alternatively, portions 630, 632 may have a common surface structure after molding, but are subsequently machined or processed (e.g., polished or chemically treated) to provide different surface properties between central portion 632 and peripheral portion 630. For example, central portion 632 may be polished after molding and/or machining to provide an optical quality window with relatively low optical aberrations, while peripheral portion 630 is not processed at all. In other embodiments, peripheral portion 630 is also polished after molding or machining, but in a way that result in a lower quality or rougher surface than central portion 632. Alternatively, peripheral portion 630 is processed after molding or machining to provide a translucent, opaque, or roughened surface, which may be used to provide different properties from central portion 632. For example, peripheral portion 630 may be roughened to scatter light and/or to provide a surface to better adhere or seal when in contact with adhesive, seal, or gasket 612. In other embodiments, peripheral portion 630 is proceed to be opaque and/or provide other favorable properties, for example, by coating or painting one or more surfaces of peripheral portion 630, or by inducing a chemical reaction, such as cross-polymerization, over all or portions of peripheral portion 630.

In certain embodiments, sample holder 610 comprises a plate comprising a plurality of through-holes that is similar or equivalent to sample holder 102. Sample holder 610 may comprise a substrate having a thickness between the opposing surfaces of sample holder 610 that is at or about 300 micrometer, wherein each through-hole may have a volume of or about 1 nanoliter, 33 nanoliters, or somewhere between 1.3 nanoliter and 33 nanoliters. Alternatively, the volume of each through-holes may be less than or equal to 1 nanoliter, for example, by decreasing the diameter of through-holes and/or the thickness of sample holder 610 substrate. For example, each through-holes may have a volume that is less than or equal to 1 nanoliter, less than or equal to 100 picoliters, less than or equal to 30 picoliters, or less than or equal to 10 picoliters. In other embodiments, the volume some or all of the through-holes is in a range from 1 nanoliter to 20 nanoliters. In certain embodiments, sample holder 610 comprises a substrate that is similar to or equal to a substrate described in copending U.S. patent application No. 61/612,087, PCT application number PCT/US2013/032002, or U.S. provisional application No. 61/774,499, all of which applications are herein incorporated by reference in their entirety. For example, through-holes 154 may have a hexagonal shape or be arranged in a hexagonal pattern. Sample holder 610 may be filled or loaded with a sample fluid including a biologic sample prior to attachment base 602. Alternatively, sample holder 610 may be filled or loaded with sample fluid including a biologic sample with sample holder 610 already attached to and/or integral with base 602. In such embodiments, a loader may be used that is similar or equivalent to one disclosed in U.S. patent application Nos. 61/612,008 or 61/723,658, both of which applications are herein incorporated by reference in their entirety.

Prior to attaching cover 604 to base 602, cavity 608 may be filled or partially filled with a fluid, such as Fluorinert™ or other suitable liquid. The inner surface of cover 604 (not visible in the figures) may include a surface structure suitable for handling or managing the distribution of bubbles formed by a liquid contained in cavity 608 during use. For example, the inner surface of cover 604 may include a surface structure similar or equivalent to that of cover 170 discussed above in reference to FIGS. 11A-11D.

Referring again to FIG. 20, sample holder 610 in the illustrated embodiment has a square shape and an overall dimension of 15 millimeter by 15 millimeter. Sample holder 610 may also include an active area, region, or zone 611 with a dimension of 13 millimeter by 13 millimeter. As used herein, the term "active area", "active region", or "active zone" means a surface area, region, or zone of sample holder 610, over which reaction regions or solution volumes (e.g., like reaction regions 154) are contained or distributed. In certain embodiments, the active area 611 may be increased to 14 millimeter by 14 millimeter or larger in order to increase the total number of reaction regions contained active area 611. Sample holder 610 may have other shapes and dimensions, for example, rectangular, triangular, circular, or some other geometric shape. The overall dimensions of sample holder 610 and active area 611 may be smaller or larger than that for the illustrated embodiment in FIG. 20, depending on the particular design parameters for a given system, assay, or experiment.

Active area 611 may comprise a plurality of reaction regions, well, vials, or through-holes (not shown; e.g., like reaction regions 154). The reaction regions may have a characteristic diameter of 75 micrometer and be distributed over active area 611 with a pitch of 125 micrometers between adjacent reaction regions. In other embodiments, the reaction regions have a characteristic diameter of that is less than or equal 75 micrometers, for example, a characteristic diameter that is less than or equal to 60 micrometers or less than or equal to 50 micrometers. In other embodiments, the reaction regions have a characteristic diameter that is less than or equal to 20 micrometers, less than or equal to 10 micrometers, less than or equal to 1 micrometer, or less than or equal to 610 nanometers. The pitch between reaction regions may be less than 125 micrometers, for example, less than or equal to 610 micrometers, less than or equal to 30 micrometers, less than or equal to 10 micrometers, or less than or equal to 1 micrometer.

In certain embodiments, sample holder 610 has a thickness between opposing top and bottom surfaces that is equal to or about 300 micrometer, so that each reaction region has a volume of about 1.3 nanoliters. Alternatively, the volume of each reaction region may be less than 1.3 nanoliters, for example, by decreasing the diameter of reaction regions and/or the thickness of sample holder 610. For example, each reaction region may have a volume that is less than or equal to 1 nanoliter, less than or equal to 610 picoliters, less than or equal to 30 picoliters, or less than or equal to 10 picoliters. In other embodiments, the volume some or all of the reaction regions are in a range from 1 nanoliter to 20 nanoliters.

In certain embodiments, the density of the reaction regions over active area 611 is at least 610 reaction regions per square millimeter. Higher densities are also anticipated. For example, a density of the reaction regions over active area 611 may be greater than or equal to 150 reaction regions per square millimeter, greater than or equal to 200 reaction regions per square millimeter, greater than or equal to 500 reaction regions per square millimeter, greater than or equal to 1,000 reaction regions per square millimeter, greater than or equal to 10,000 reaction regions per square millimeter, or greater than or equal to 1,000,000 reaction regions per square millimeter. Advantageously, all the reaction regions in active area 611 may be simultaneously imaged and analyzed by an optical system. In certain embodiments, active area 611 imaged and analyzed by the optical system comprises at least 12,000 reaction regions. In other embodiments, active area 611 imaged and analyzed by the optical system comprises at least 15,000, at least 20,000, at least 30,000, at least 610,000, at least 1,000,000 reaction regions, or at least 10,000,000 reaction regions.

Where appropriate, case 600 and its associated elements may incorporate features, embodiments, dimensions, and/or functions discussed above in relation to case 150, and vice versa. For instance, case 600 and/or sample holder 610 may be configure to reduce or eliminate the amount or effect of bubbles produced during thermocycling, as discussed above in relation to case 150 and sample holder 102.

Figure 23:
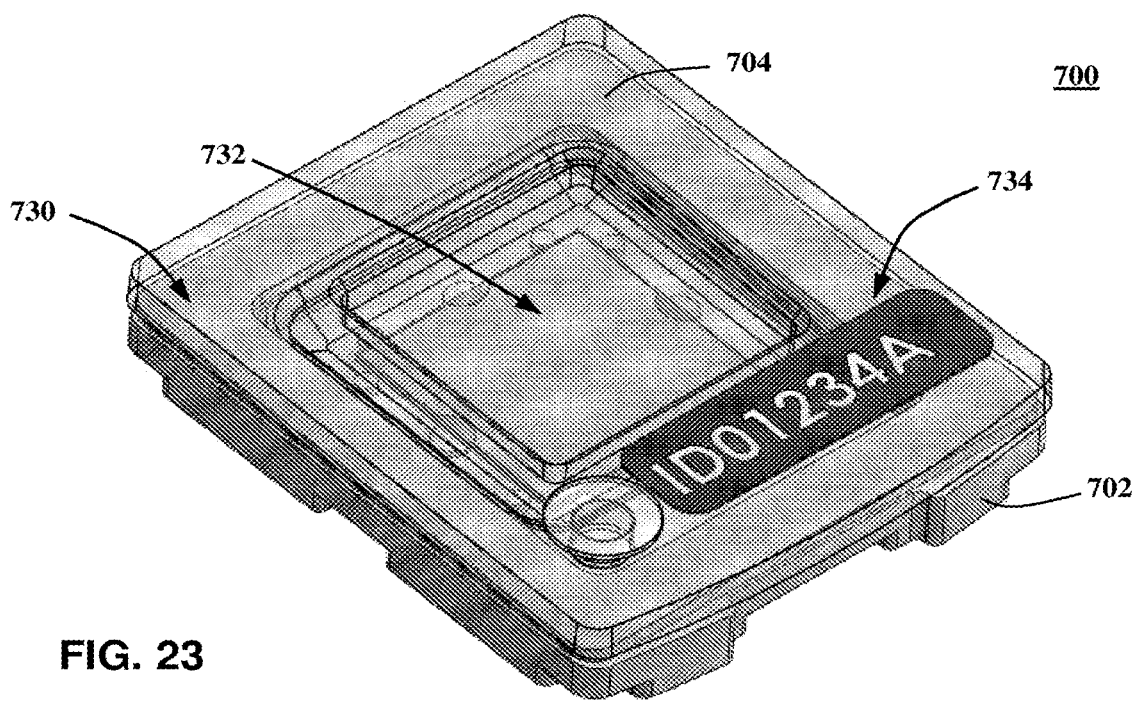
FIG. 23 is a perspective view of a case according to an embodiment of the present invention.
Figure 24:
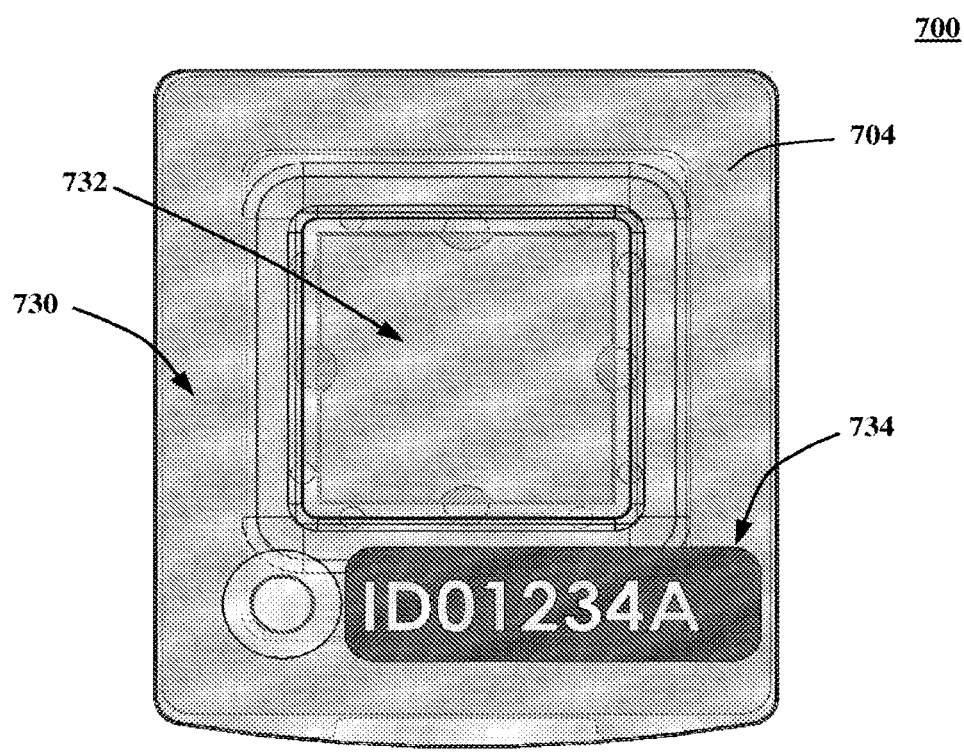
FIG. 24 is a front view of the case shown in FIG. 23.
Figure 25:
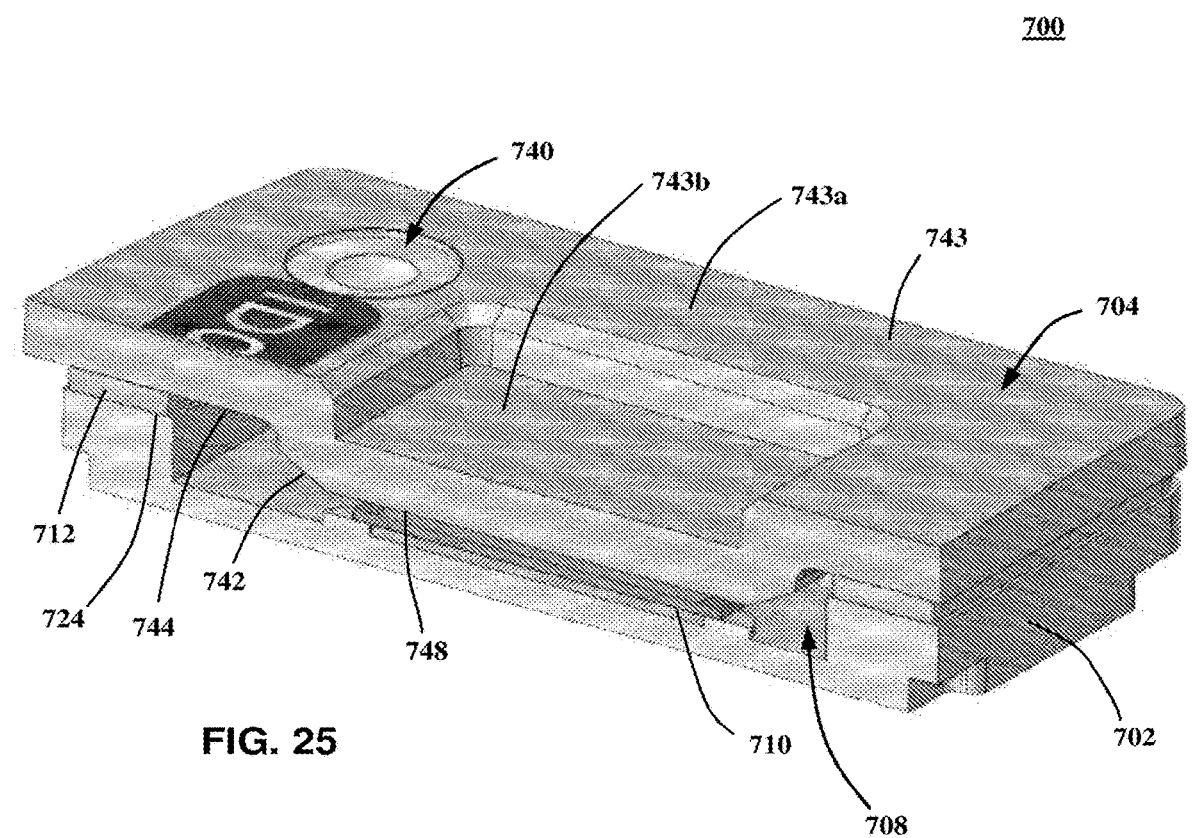
FIG. 25 is a cross-sectional view of the base shown in FIG. 23.

Referring to FIGS. 23-25, in certain embodiments an enclosure, housing, or case 700 comprises a base 702 and a cover or lid 704 configured to sealably engage base 702. Base 702 and cover 704 may be joined together to form a cavity or chamber 708, which may receive or contain a sample holder, substrate, planar member, or plate 710. Sample holder 710 may be part of base 702, or may be separate and/or distinct from base 702 and be configured to be mounted or held by base 702. Case 700 may further comprise an adhesive, seal, or gasket 712 disposed between base 702 and cover 704, for example, to seal or isolate cavity 708 and sample holder 710 from an outside environment.

Sample holder 710 may be constructed, loaded, and attached or joined to base 702 as discussed above in relation to sample holder 610. In certain embodiments, sample holder 710 comprises a plate comprising a plurality of through-holes and including one or more features or embodiments of sample holders 102, 610 discussed above. Sample holder 710 may be filled or loaded with a sample fluid including a biologic sample prior to attachment base 702. Alternatively, sample holder 710 may be filled or loaded with sample fluid including a biologic sample with sample holder 710 already attached to and/or integral with base 702. In such embodiments, a loader may be used that is similar or equivalent to one disclosed in U.S. patent application Nos. 61/612,008 or 61/723,758, both of which applications are herein incorporated by reference in their entirety.

Figure 26:
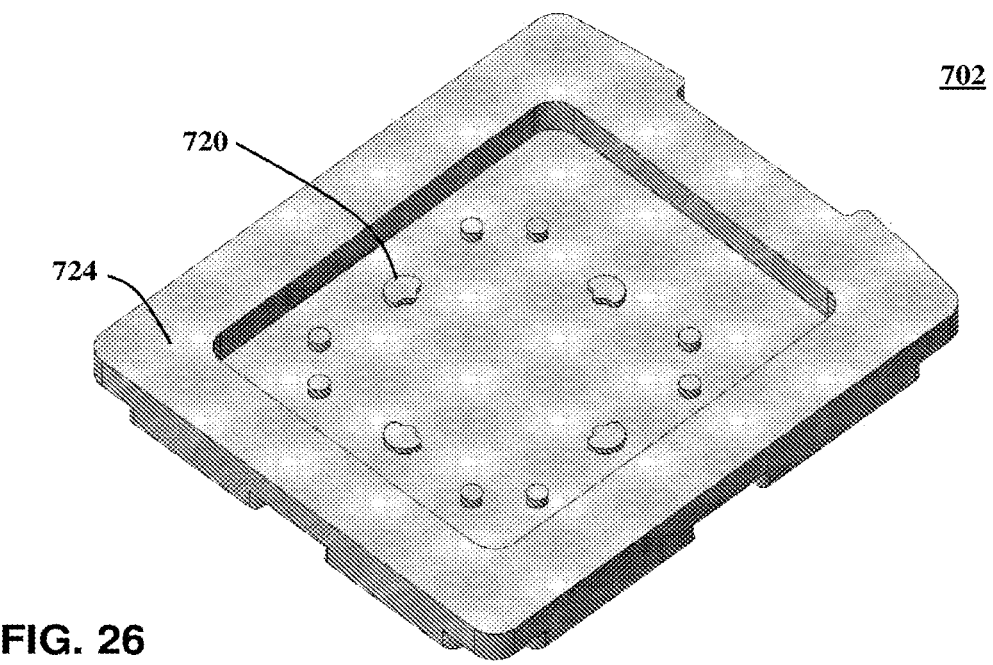
FIG. 26 is a perspective view of the base shown in case of FIG. 23 without a sample plate.
Figure 27:
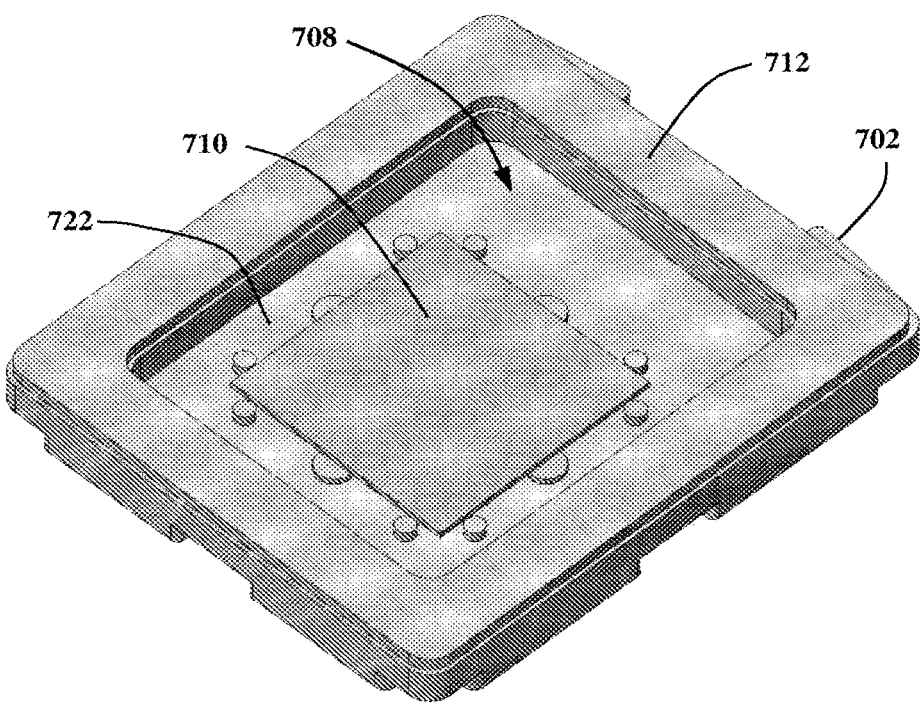
FIG. 27 is a perspective view of the base shown in case of FIG. 26 with a sample plate and an added seal.

Referring to FIGS. 26 and 27, base 702 may comprise a plurality of bosses, tabs, staking sites, and/or support pads 720 that are configured to hold and/or locate sample holder 710 within base 702 and cavity 708. Tabs 720 may be configured as, or similar to, tabs 620. Base 702 may be configured to receive seal 712, for example, in the form of a gasket or adhesive configured to seal cavity 708. Seal 712 may include one or more adhesive materials configured to join, seal, and/or secure cover 704 to base 702. In certain embodiments, the one or more adhesive materials are configured to provide a permanent or secure connection of cover 704 to base 702 so as to isolate the sample contained in sample holder 710 from the ambient environment, for example, to reduce or eliminate the release of high-copy DNA amplicons into a surrounding lab environment produced by a PCR or similar amplification process, thus reducing or minimizing environmental exposure to contaminants.

In certain embodiments, seal 712 provide a fluid-tight seal (e.g., airtight or liquid-tight seal) of cavity 708. For example, seal 712 may be configured to provide a fluid tight seal such that a liquid (e.g., a Fluorinert™) inside cavity 708 does not leak out during use (e.g., during thermal cycling of the sample in sample holder 710 in a PCR experiment or assay). In the illustrated embodiment, base 702 comprises a surface or face 724 configured to receive seal 712. Surface 724 may be flat, as shown in FIG. 26. Alternatively, surface 724 may include an inset groove or channel configured to contain seal 712, for example, as shown groove 624a shown in FIG. 22 for base 602.

Figure 28:
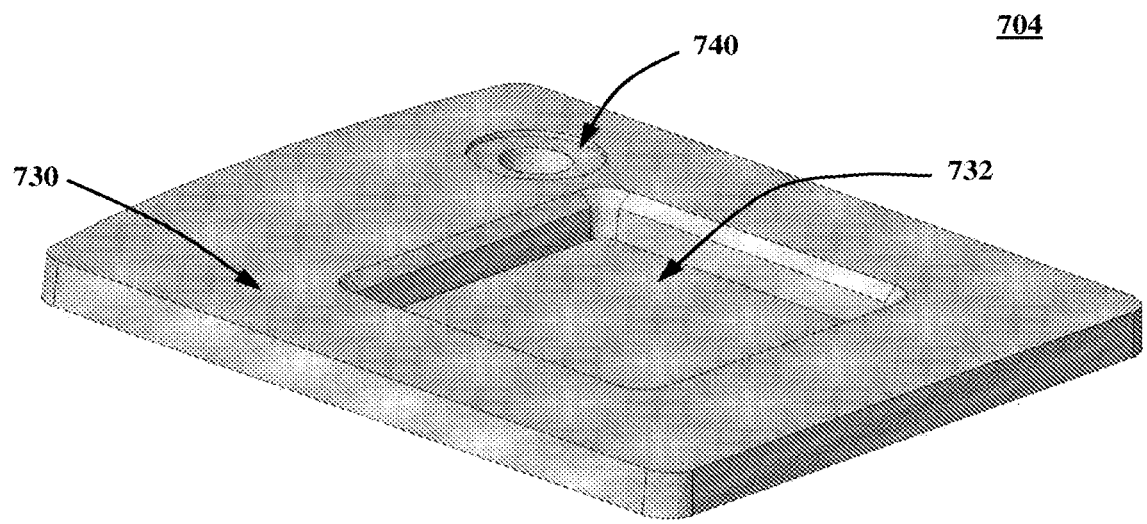
FIG. 28 is a front, perspective view of the cover shown in case of FIG. 23.
Figure 29:
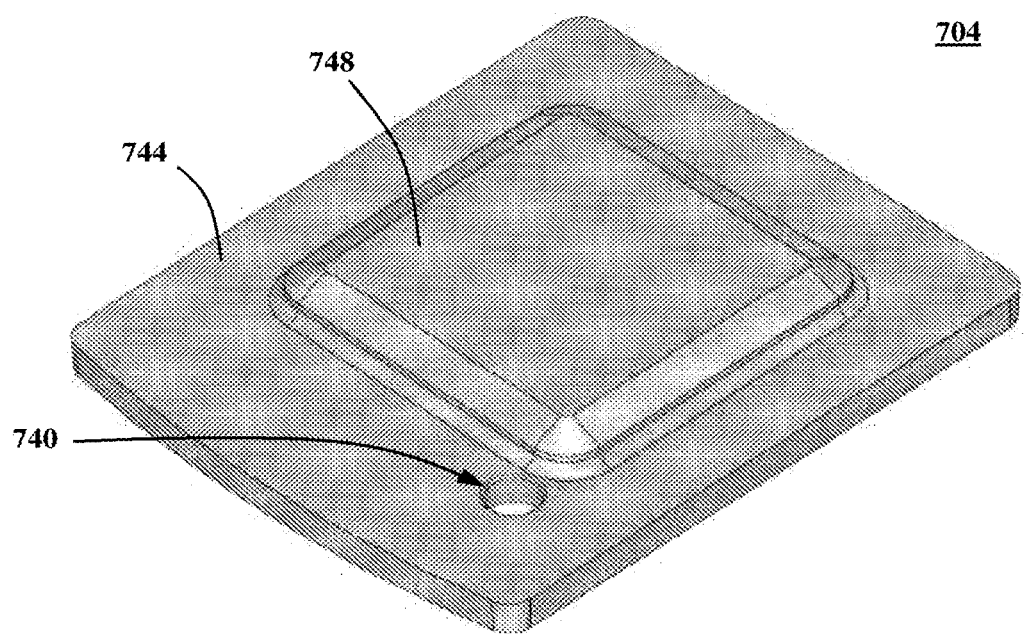
FIG. 29 is a perspective view of the cover shown in case of FIG. 23 showing an inner surface of the cover.

Referring to again FIGS. 23 and 24, cover 704 comprises a peripheral portion 730, a central portion 732, and a label area 734 configured to receive a separate label containing alphanumeric characters, barcode, QR code (quick response code), or other type of marks or indicia. Portions 730, 732 and label 734 may include various aspects and embodiments discussed above in relation to portions 630, 632 and label 634 discussed above in relation to cover 604. With additional reference to FIGS. 28-29, cover 704 also comprises an inner surface or face 742 and an outer surface or face 743. Inner surface 742 may be configured to engage or interface with surface 724 of base 702 and/or seal 712. Inner surface 742 may comprise a base or floor area 744 and protruding or projecting portion 748 that is offset from base area 744 and is located near sample holder 710 when cover 704 is attached to base 702. A gap between protruding portion 748 and sample holder 710 may be selected to reduce convective currents over sample holder 710 and/or to reduce thermal non-uniformity over sample holder 710. Outer surface 743 includes a plateau or reference area 743a that may flat or nominally flat. Outer surface 743 may also include a central area 743b that is located over sample holder 710 when cover 704 is attached to base 702. Relative to reference area 743a, central area 743b may be indented or offset toward inner surface 742. Alternatively, areas 743a and 743b may form a contiguous and/or flat surface, for example, to provide greater rigidity.

Base area 744 of inner surface 742 and/or reference area 743a of outer surface 743 may include fill port 740 configured for introducing a liquid into cavity 708 formed after attachment of cover 704 to base 702. The fluid introduced may entirely fill or partially fill cavity 708 with a liquid configured to reduce or prevent evaporation of sample from sample holder 710, for example, during thermal cycling in a PCR assay or experiment. Fill port 740 may be configured so that air or gas bubbles formed during filling of cavity 708 tend to migrate, for example due to buoyancy effects, away from protruding portion 748, toward base area 744, and out through fill port 740. After the addition of fluid into cavity 708, fill port 740 may be sealed, for example, using a plug. In certain embodiments, the plug comprises an epoxy or other suitable material that may be hardened after application, for example, using ultraviolet radiation. Thus, fill port 740 may be advantageously located on cover 704 in order facilitate the purging of entrapped gas or bubbles in cavity 708 while case 700 is oriented horizontally and in the same orientation it has during an experiment or assay.

Where appropriate, case 700 and its associated elements may incorporate features, embodiments, dimensions, and/or functions discussed above in relation to case 150 and/or case 600, and vice versa. For instance, case 700 and/or sample holder 710 may be configure to reduce or eliminate the amount or effect of bubbles produced during thermocycling, as discussed above in relation to case 150 and sample holder 102.

Figure 30:
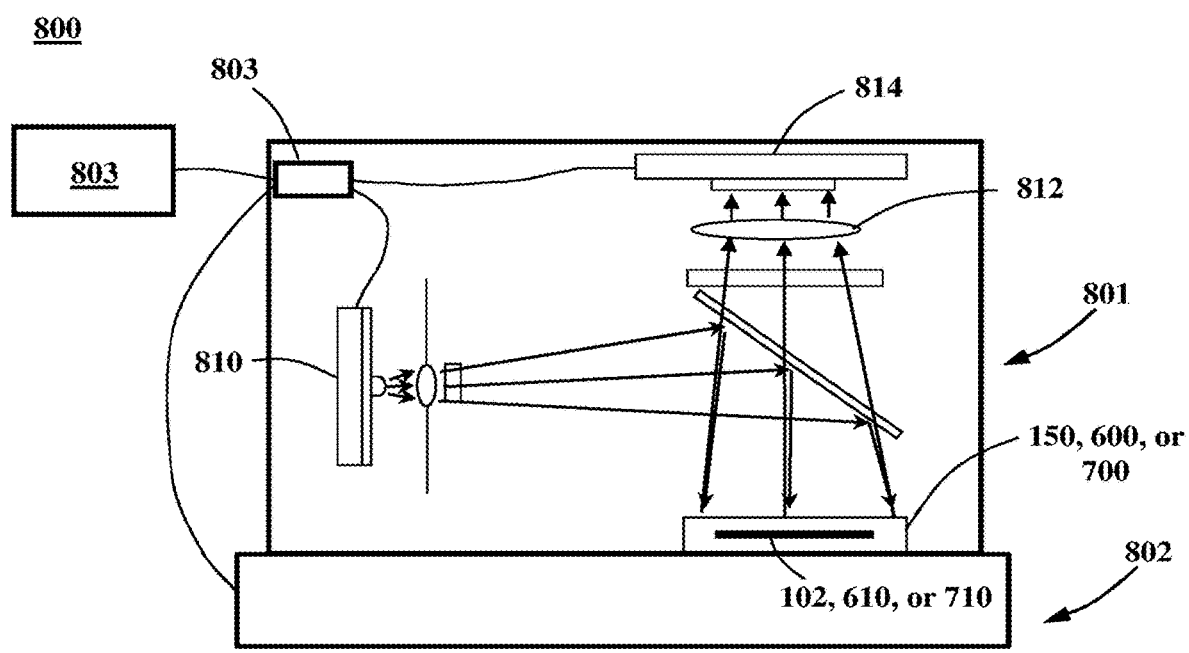
FIG. 30 is a schematic of an optical reader used in conjunction with a case according to embodiments of the present invention.

Referring to FIG. 30, case 600, 700 may be used in conjunction with a system 800, which may be equivalent or similar to that disclosed in U.S. patent application No. 61/659,029 or PCT patent application number PCT/US2013/031890, each of which applications are herein incorporated by reference in their entirety. System 800 may include an optical system or reader 801 may comprising a light source 810, the case 150, 600 or 700 with sample holder 102, 610 or 710, an imaging lens 812, a sensor 814, and optics for directing light from light source 810 onto sample holder 102, 610 or 710 and for directing light emitted by samples contained in sample holder 102, 610 or 710 to sensor 814. System 800 may also include a thermal controller 802 and one or more processors 803 to operating the system 801 and/or thermal controller 802.

In certain embodiments, system 800 does not include thermal controller 802, or thermal controller 802 comprises a separate instrument or system that is not contained within the same housing or instrument as optical system 801. For example, optical system 801 may be configured to receive a case 150, 600 or 700 and/or sample holder 102, 610 or 710 that was thermocycled in a separate thermal controller, such as a PCR thermocycler. Optical system 801 may be subsequently used to perform an endpoint PCR or dPCR experiment or assay. In certain embodiments, the separate thermal control system is configured to process a plurality of chips or plates, for example, in the form of case 150, 600 or 700, or the like. In such embodiments, optical system 801 may be configured to receive one or more of the plurality of cases 150, 600 or 700 in order to perform a dPCR experiment or assay. The one or more processors 803 may be used to perform a dPCR analysis based on data from sample holder 102, 610 or 710.

Figure 31:
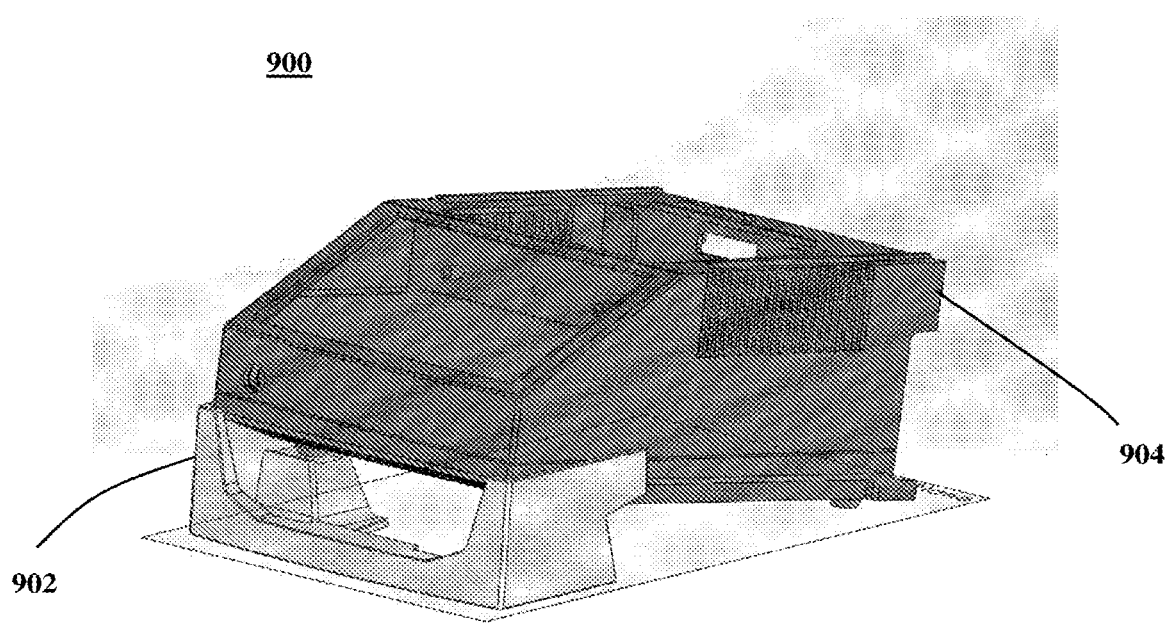
FIG. 31 is a perspective view of an offset member and housing according to an embodiment.
Figure 32:
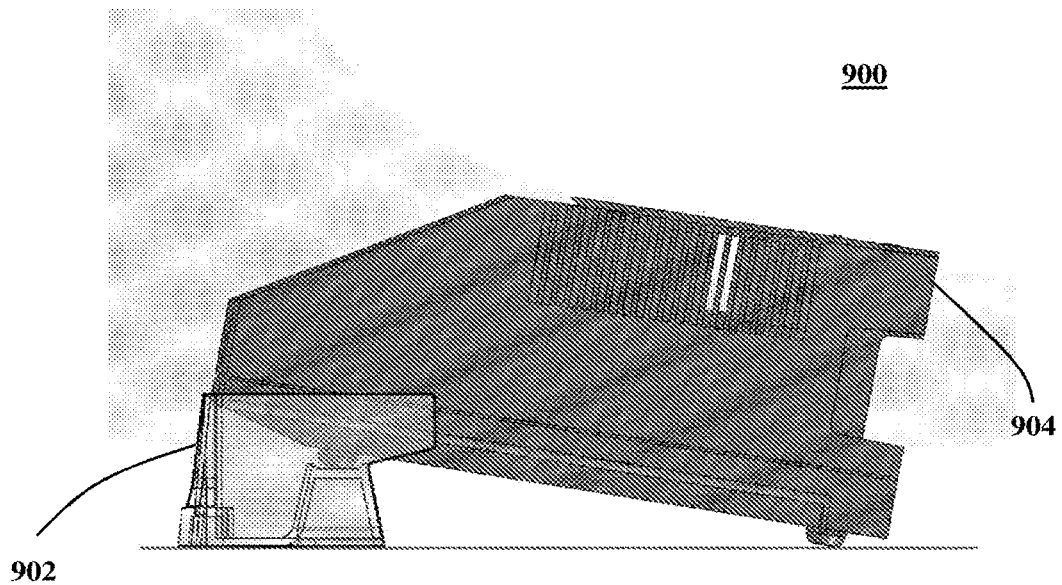
FIG. 32 is a side view of an offset member and housing according to an embodiment.

Referring to FIGS. 31 and 32, at least some of the elements of a system 900 for processing a plurality of biological samples according to embodiments of the present invention are shown. The system 900 comprises an offset member 902 and a housing 904. The housing 904 may include a support to hold a case according to any of the embodiments of these elements disclosed herein. In certain embodiments, the offset member 902 engages the housing 904 during use to maintain at least one of a support, case, or substrate according to an embodiment of the invention at the positive angle during an assay or reaction of one or more biological samples. In other embodiments, the offset member 902 is located within the housing 904 and engages a support, case, or substrate according to an embodiment of the invention during use to maintain the at least one surface at the positive angle during the assay or reaction.

EXAMPLE

Various test cases and sample holders similar to case 700 and sample holder 710 were constructed study the problem of cross-contamination during thermocycling due to the formation of bubbles during thermocycling. The test sample holders each comprised approximately 20,000 through-holes having a hexagonal cross-section, each through-hole having a major diameter of about 60 micrometers. The through-holes of each test sample holder were arranged in a hexagonal pattern at a minimum distance between adjacent through-hole of 72 micrometers. Each test sample holder was mounted in a test case so that the distance between the inside bottom of the test case and the bottom of the test sample holder was approximately 300 micrometers. The through-holes of the test sample holders were filled with a test solution and enclosed inside the test case by attaching a cover to a base of the test case. The cavity in each test case was then filled with Fluorinert and sealed.

Various of the test cases were processed in a thermocycler over a cycling temperature range between 60 degrees Centigrade and 95 degrees Centigrade. During thermocycling, test cases were tilted at different angles relative to a horizontal plane. The sample holder with then evaluated for the amount of cross-contamination. The following results were obtained.

| Angle | Amount of Contamination |
| --- | --- |
| 0 degrees | significant |
| 5 degrees | reduced |
| 10 degrees | none or undetectable |
| 15 degrees | none or undetectable |

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiments disclosed. On the contrary, the intention is to cover modifications and alternate constructions coming within the spirit and scope of the invention as generally expressed by the following claims, which particularly point out and distinctly claim the subject matter of the invention.

Exemplary systems for methods related to the various embodiments described in this document include those described in following list of U.S. and PCT applications:

Life Technologies Docket Number LT00655 PRO, which is U.S. provisional application No. 61/612,087, filed on Mar. 16, 2012; and Life Technologies Docket Number LT00655 PRO 2, which is U.S. provisional application No. 61/723,759, filed on Nov. 7, 2012; and Life Technologies Docket Number LT00656 PRO, which is U.S. provisional application No. 61/612,005, filed on Mar. 16, 2012; and Life Technologies Docket Number LT00657 PRO, which is U.S. provisional application No. 61/612,008, filed on Mar. 16, 2012; and Life Technologies Docket Number LT00657 PRO 2, which is U.S. provisional application No. 61/723,658, filed on Nov. 7, 2012; and Life Technologies Docket Number LT00668 PRO, which is U.S. provisional application No. 61/723,738, filed on Nov. 7, 2012; and Life Technologies Docket Number LT00699 PRO, which is U.S. provisional application No. 61/659,029, filed on Jun. 13, 2012; and Life Technologies Docket Number LT00749 PRO, which is U.S. provisional application No. 61/723,710, filed on Nov. 7, 2012; and Life Technologies Docket Number LT00749 PRO 2, which is U.S. provisional application No. 61/774,499, filed on Mar. 7, 2013; and Life Technologies Docket Number LT00746 DES, which is U.S. design application number 29/436,636, filed on Nov. 7, 2012; and Life Technologies Docket Number LT00655 PCT, which is PCT application number PCT/US2013/032002, filed Mar. 15, 2013; and Life Technologies Docket Number LT00656 PCT, which is PCT application number PCT/US2013/032420, filed Mar. 15, 2013; and Life Technologies Docket Number LT00657 PCT, which is PCT application number PCT/US2013/032107, filed Mar. 15, 2013; and Life Technologies Docket Number LT00668 PCT, which is PCT application number PCT/US2013/032242, filed Mar. 15, 2013; and Life Technologies Docket Number LT00699 PCT, which is PCT application number PCT/US2013/031890, filed Mar. 15, 2013.

All of these applications are also incorporated herein in their entirety by reference.

What is claimed is:

1. A system for processing a plurality of biological samples, comprising:
   a case comprising:
      a substrate located within an inner chamber of the case, the substrate comprising a surface and a plurality of through-holes disposed along the surface, the plurality of through-holes configured to contain one or more biological samples;
   a thermal cycling instrument comprising:
      a housing,
      a support disposed within the housing and configured to receive the case,
      a temperature controller operably coupled to control a temperature of the support when the case is received on the support, and
      an offset member configured to maintain the surface of the substrate at an angle of at least 5 degrees relative to a horizontal plane when the case is received on the support to perform a thermal cycling assay.

2. The system of claim 1, wherein the case further comprises a base.

3. The system of claim 2, wherein a cover is disposed over a portion of the base, the cover and the base forming the inner chamber.

4. The system of claim 1, further comprising a sealing fluid disposed within the inner chamber and covering the surface of the substrate.

5. The system of claim 1, wherein the offset member is coupled to the instrument housing.

6. The system of claim 5, wherein the offset member is arranged to position the housing in a tilted position to maintain the surface at the angle during the thermal cycling assay.

7. The system of claim 1, wherein the angle of at least 5 degrees is an amount sufficient to prevent a transfer of sample solution between any pair of adjacent through-holes of the plurality of through-holes during the thermal cycling assay.

8. The system of claim 1, wherein the thermal cycling assay is a polymerase chain reaction assay.

9. The system of claim 1, wherein the angle is an amount sufficient to move a gas bubble formed between the substrate and the case toward an end of the case.

10. A system for processing a plurality of biological samples, comprising:
    a case comprising:
       an inner chamber, and
       a substrate located within the inner chamber, the substrate containing a plurality of isolated through-holes configured to contain one or more biological samples;
    a support configured to hold the case to perform an assay or reaction of the one or more biological samples;
    a temperature controller configured to control a temperature of at least one of the support, the case, and one or more biological samples when contained in the plurality of through-holes; and
    an offset member configured to maintain a surface of the substrate at an angle of at least 5 degrees relative to a horizontal plane when the case is received on the support to perform the assay or reaction.

11. The system of claim 10, further comprising a housing enclosing the support, wherein the offset member is coupled to the housing.

12. The system of claim 11, wherein the offset member is arranged to position the housing in a tilted position to maintain a surface of the substrate at the angle during the assay or reaction.

13. The system of claim 10, wherein the angle of at least 5 degrees is an amount sufficient to prevent a transfer of sample solution between any pair of adjacent through-holes of the plurality of through-holes during the assay or reaction.

14. The system of claim 10, wherein the assay or reaction is a polymerase chain reaction assay.

15. A method of processing a plurality of biological samples disposed along a surface of a substrate, comprising:
    disposing a case thermal contact with a support in a housing of a thermal cycling instrument, wherein a substrate comprising a plurality of through-holes containing a plurality of biological samples is disposed within an inner chamber of the case;
    controlling a temperature of the support to perform a thermal cycling assay on the plurality of biological samples; and
    maintaining the surface of the substrate at an angle of at least 5 degrees relative to a horizontal plane while performing the thermal cycling assay.

16. The method of claim 15, further comprising arranging an offset member to position the housing in a tilted position to maintain the surface of the substrate at the angle during the thermal cycling assay.

17. The method of claim 15, wherein maintaining the surface of the substrate at the angle of at least 5 degrees prevents of the biological samples from migrating between the through-holes.

18. The method of claim 15, wherein the thermal cycling assay is a polymerase chain reaction assay.

19. The method of claim 15, wherein the angle is an amount sufficient to move a gas bubble formed between the substrate and the case toward an end of the case.

20. The method of claim 15, further comprising monitoring the plurality of biological samples, via an optical system, while performing the thermal cycling assay.

* * * * *